(12) United States Patent
Ludwig

(10) Patent No.: US 8,560,130 B2
(45) Date of Patent: Oct. 15, 2013

(54) SOFTWARE CONTROLLED LAB-ON-A-CHIP EMULATION

(75) Inventor: Lester F. Ludwig, Redwood Shores, CA (US)

(73) Assignee: Lester F. Ludwig, Belmont, CA (US)

( * ) Notice: Subject to any disclaimer, the term of this patent is extended or adjusted under 35 U.S.C. 154(b) by 622 days.

(21) Appl. No.: 12/328,713

(22) Filed: Dec. 4, 2008

(65) Prior Publication Data
US 2009/0326903 A1   Dec. 31, 2009

Related U.S. Application Data

(60) Provisional application No. 61/005,369, filed on Dec. 4, 2007.

(51) Int. Cl.
*G05D 7/00* (2006.01)
(52) U.S. Cl.
USPC ............................................ 700/282; 700/19
(58) Field of Classification Search
USPC ...................................... 700/275, 282; 703/23
See application file for complete search history.

(56) References Cited

U.S. PATENT DOCUMENTS

| | | | | |
|---|---|---|---|---|
| 4,787,591 | A * | 11/1988 | Villacorta | 248/316.7 |
| 5,530,988 | A * | 7/1996 | McQuillan | 15/406 |
| 5,577,890 | A * | 11/1996 | Nielsen et al. | 417/44.2 |
| 6,681,616 | B2 * | 1/2004 | Spaid et al. | 73/54.07 |
| 7,002,311 | B2 * | 2/2006 | Strike et al. | 318/400.13 |
| 2003/0087300 | A1 * | 5/2003 | Knapp et al. | 435/6 |
| 2007/0036024 | A1 * | 2/2007 | Kubala et al. | 366/163.2 |
| 2008/0223721 | A1 | 9/2008 | Cohen et al. | |
| 2009/0121476 | A1 | 5/2009 | Malito et al. | |
| 2009/0202731 | A1 * | 8/2009 | Kazkaz et al. | 427/421.1 |

OTHER PUBLICATIONS

DS1920 Temperature iButton, Dallas Semiconductor Corporation 1997.*
Bernhard et al., "Design and Rapid Prototyping of Thin-Film Laminate-Based Microfluidic Devices", Biomedical Microdevices, Kluwer Academic Publishers, 2001.*
Takahashi et al., "A 40-Gb/s Self-Clocked Bidirectional Serial/Parallel Converter for Asynchronous Label Swapping", IEEE, Mar. 2007.*

(Continued)

*Primary Examiner* — Carlos Ortiz Rodriguez
(74) *Attorney, Agent, or Firm* — Procopio, Cory, Hargreaves & Savitch LLP

(57) ABSTRACT

A software-controlled chemical process emulation system and environment having individually-addressable and/or group-addressable software-controlled chemical system processing modules, software-controlled chemical system handling modules, and related components. The software-controlled modules may be designed and interconnected to emulate various fixed, configurable, and reconfigurable "Lab-on-a-Chip" ("LoC") devices. The software-controlled modules may be designed as separate units with well-defined ports and interfaces that can be used in the construction of larger systems. Alternatively, the software-controlled modules may be integrated into more complex subsystems that can be used in similar or other ways. These aspects may be used to design a LoC device, develop software for the operation of a LoC device, or may be used together with actual LoC devices as part of a larger system. Some applications may be used to implement laboratory automation features in experimental set-ups and laboratory-scale chemical production.

20 Claims, 33 Drawing Sheets

(56) References Cited

OTHER PUBLICATIONS

Fluidic Valves for Variable-Configuration Gas Treatment, V. Tesar, Institution of Chemical Engineers, Trans IChemE, Part A, Sep. 2005, Chemical Engineering Research and Design, 83(A9): 1111-1121, available at http://eprints.whiterose.ac.uk/758/1/tesarv6.pdf.

Development of a Microfluidic Unit for Sequencing Fluid Samples for Composition Analysis, V. Tesař*, J. R. Tippetts, Y. Y. LOWand R. W. K. Allen, Institution of Chemical Engineers, Trans IChemE, Part A, Jun. 2004, Chemical Engineering Research and Design, 82(A6): 708-718, available at http://eprints.whiterose.ac.uk/468/1/tesarv2.pdf.

Sampling by Fluidics and Microfluidics, V. Tesař, Acta Polytechnica vol. 42 No. Feb. 2002.

Development of a MEMS Microvalve Array for Fluid Flow Control, Nelsimar Vandelli, Donald Wroblewski, Margo Velonis, and Thomas Bifano, Journal of Microelectromechanical Systems, vol. 7, No. 4, Dec. 1998, available at http://sws1.bu.edu/bifano/PDF_files/23_Flow.pdf.

Development of a Rapid-Response Flow-Control System Using MEMS Microvalve Arrays, John Collier, Donald Wroblewski, and Thomas Bifano, Journal of Microelectromechanical Systems, vol. 13, No. 6, Dec. 2004, available at http://128.197.153.21/tgb/PDF_files/Valves.pdf.

A Novel Pressure Balanced Microfluidic Valve, J. M. Quero, A. Luque, L. G. Franquelo, Proc. ISCAS 2002, May 26-29, available at http://woody.us.es/~aluque/doc/pressure_balanced_microvalve.pdf.

Fabrication of Polysilicon Micro Valve Array, Jermaine White, 22rd Annual Microelectronic Engineering Conference, May 2004, available at http://www.rit.edu/~w-ue/ameccontent/17_JWhite.pdf.

Parker R-max™ Stream Switching System, Parker Instrumentation, Catalog 4140-R, Revised, Jun. 2002, available at http://www.plesner.as/mod/products/upload/4140-R.pdf.

Fast Switching Valves: Ultra Fast and Highly Repeatable, FESTO Corp, Info 96 207 US, Jun. 2005, available at http://www.zycon.com/Literature/219948/75280/Info207_FastSwitchingV.pdf.

Flow Selection Valves: Series 105T Valve, Bio-Chem Fluidics, 2010, available at https://www.biochemfluidics.com/cart/store/comersus_listOneCategory.asp?idCategory=393.

Flow Selection Valves: Series 080T Valve, Bio-Chem Fluidics, 2010, available at https://www.biochemfluidics.com/cart/store/comersus_listOneCategory.asp?idCategoiy=392.

Cheminert® Valves for Flow Injection Analysis, FIAlab Instruments, 2010, available at http://www.flowinjection.com/valves.html.

Solenoid valves and eletric valve, Peter Paul Electronics Co., Inc., 2010, available at http://www.peterpaul.com/whats_new_display2.php4?cat_id=6.

Gems Predyne Pneumatic Solenoid Valves & Miniature Solenoid Valves: general-purpose-valves, Gems Sensors & Controls, 2010, available at http://www.gemssensors.com/Search.aspx?q=general-purpose-valves.

Gems Predyne Pneumatic Solenoid Valves & Miniature Solenoid Valves: isolation-valves, Gems Sensors & Controls, 2010, available at http://www.gemssensors.com/Search.aspx?q=isolation-valves.

1200 Series Valve Solutions, Agilent Technologies, 2000-2010, available at http://www.chem.agilent.com/en-us/products/instruments/lc/1200seriesvalvesolutions/pages/default.aspx.

Valve matrix takes squeeze out of juice production, Prepared Foods, Oct. 1997, available at http://findarticles.com/p/articles/mi_m3289/is_n11_v166/ai_20224164/.

LG16, Media Isolated Microfluidic Flow Sensor, www.sensirion.com. Apr. 2009, V1.1., available at http://www.sensirion.com/en/pdf/product_information/Datasheet_Liquid_Flow_Sensor_LG16_E.pdf.

* cited by examiner

2:1 INPUT 8-VALVE COMPLEX n:1 INPUT 11-VALVE COMPLEX n : n INPUT 14-VALVE COMPLEX

1:4 OUTPUT (7 + 1) VALVE COMPLEX

4:1 INPUT TANDEM VALVE COMPLEX

4:1 TANDEM OUTPUT VALVE COMPLEX

GAS ROUTING 5-VALVE SLAVE COMPLEX

GAS ROUTING 7-VALVE SLAVE COMPLEX

3:1 BLOCK VALVE

4:1 BLOCK VALVE

6:1 + 1 BLOCK VALVE

6:1 BLOCK MANIFOLD VALVE

VARIABLE SPEED PUMP MODULE
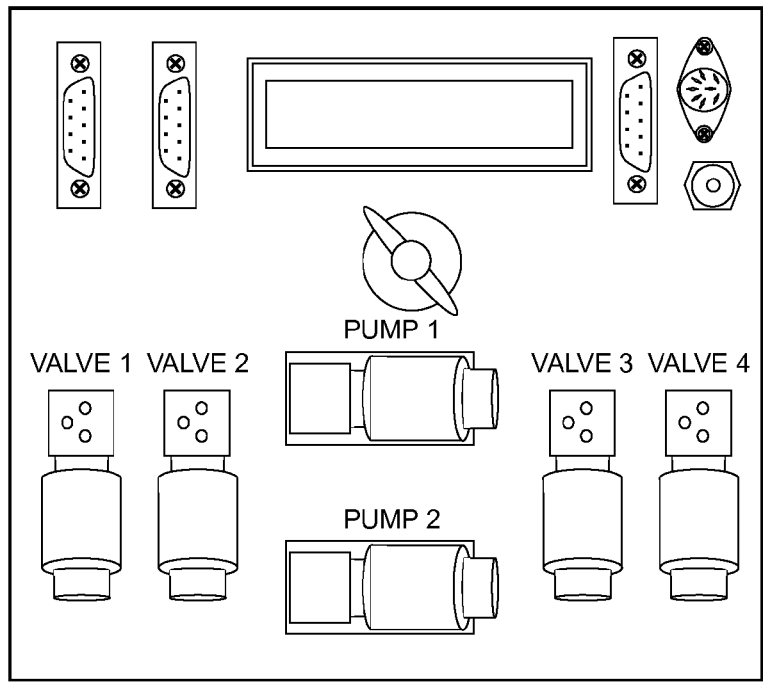
Figure 24
CHEMICAL REACTOR MODULE
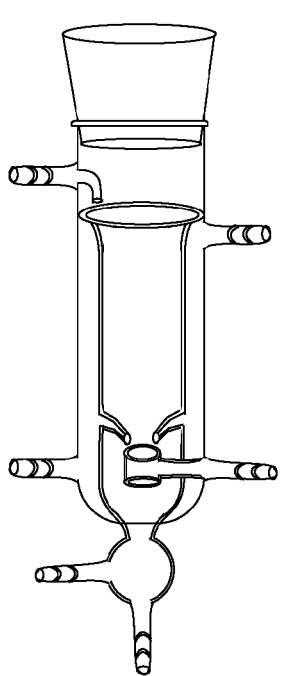
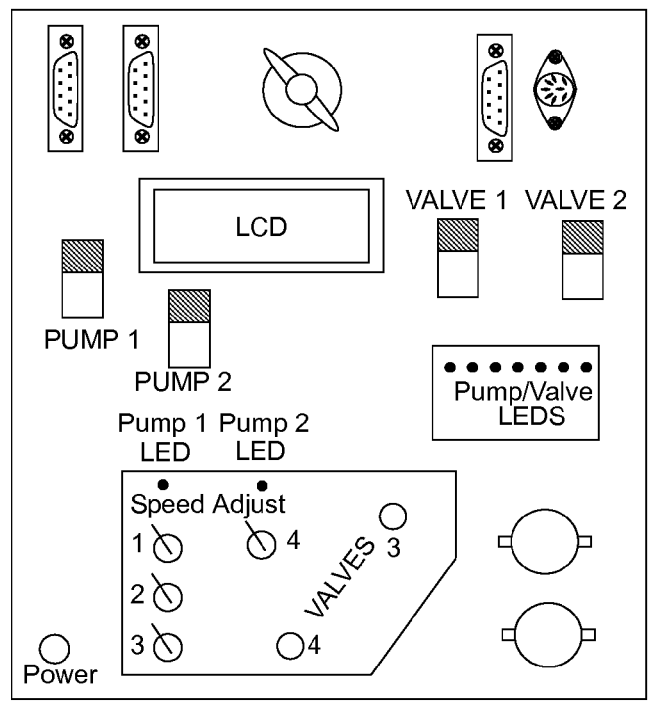
Figure 25a
Figure 25b

SOFTWARE CONTROLLED LAB-ON-A-CHIP EMULATION

CROSS-REFERENCE TO RELATED APPLICATIONS

Pursuant to 35 U.S.C. Section 119(e), this application claims benefit of priority from provisional patent application Ser. No. 61/005,369, filed Dec. 4, 2007, the contents of which are hereby incorporated by reference herein in their entirety.

FIELD OF THE INVENTION

The present invention generally pertains to controlled chemical processing, and in particular to components for software-controlled emulation of fixed, configurable, and reconfigurable devices such as a Lab-on-a-chip (LoC).

SUMMARY OF THE INVENTION

Features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

In accordance with an embodiment, a system for emulating a lab-on-a-chip design includes a plurality of electrically-powered controllable chemical process modules, each chemical process module comprising at least one chemical flow input port, at least one chemical flow output port, at least one communications interface employing a communications protocol and receiving communications signals, and at least one electrically controllable element responsive to received communications signals. The system further includes chemical flow interconnections among at least two of the plurality of controllable chemical process modules, the chemical flow interconnections comprising a chemical flow path connecting the chemical flow output port of a first chemical process module with a second chemical process module. Another feature includes a network for carrying communications signals, the network connecting with the control interface of the first chemical process module and with the second chemical process module, the network additionally providing a connection to a data processor, the data processor for executing algorithms for controlling the at least one electrically controllable element comprised by the first and second chemical process modules. The system is typically configured so that an algorithm executing in the data processor can control the plurality of electrically-powered controllable chemical process modules to emulate aspects of the operation of a design for a physically smaller lab-on-a-chip system.

These and other embodiments will also become readily apparent to those skilled in the art from the following detailed description of the embodiments having reference to the attached figures, the invention not being limited to any particular embodiment disclosed.

BRIEF DESCRIPTION OF THE DRAWINGS

The above and other aspects, features, and advantages of the present invention will become more apparent upon consideration of the following description of preferred embodiments, taken in conjunction with the accompanying drawing figures.

FIGS. 10b and 10c show an exemplary (n=4) electronic implementation of the valve complex of FIG. 10a.

FIGS. 11b-11c show an exemplary (n=4) electronic implementation of the valve complex of FIG. 11a.

FIG. 12b shows an exemplary electronic implementation of the valve complex of FIG. 12a.

FIG. 13b shows an exemplary electronic implementation of the valve complex of FIG. 13a.

FIG. 14b shows an exemplary electronic implementation of the valve complex of FIG. 14a.

FIG. 15b shows an exemplary slaved electronic implementation of the arrangement of FIG. 15a.

FIG. 16b shows an exemplary slaved electronic implementation of the arrangement of FIG. 16a.

FIG. 24 shows an exemplary laboratory lattice-scale embodiment of variable speed pump module comprising two variable-speed low-voltage DC motor diaphragm pumps and four chaperoning routing/switch valves.

FIG. 25a shows an exemplary glassware element that can be used in a laboratory lattice-scale implementation of a chemical reactor module.

FIG. 25b shows an exemplary laboratory lattice-scale mechanical and electronic support implementation for the chemical reactor module based on the exemplary glassware element of FIG. 25a.

FIG. 25c depicts an exemplary hand-configurable laboratory lattice-scale implementation combining the exemplary glassware element of FIG. 25a with the arrangement of FIG. 25b in a style similar to that of FIG. 8a.

DETAILED DESCRIPTION OF THE PREFERRED EMBODIMENTS

In the following detailed description, reference is made to the accompanying drawing figures which form a part hereof, and which show by way of illustration specific embodiments of the invention. It is to be understood by those of ordinary skill in this technological field that other embodiments may be utilized, and structural, electrical, as well as procedural changes may be made without departing from the scope of the present invention. Wherever possible, the same reference numbers will be used throughout the drawings to refer to the same or similar parts.

Figure 1:
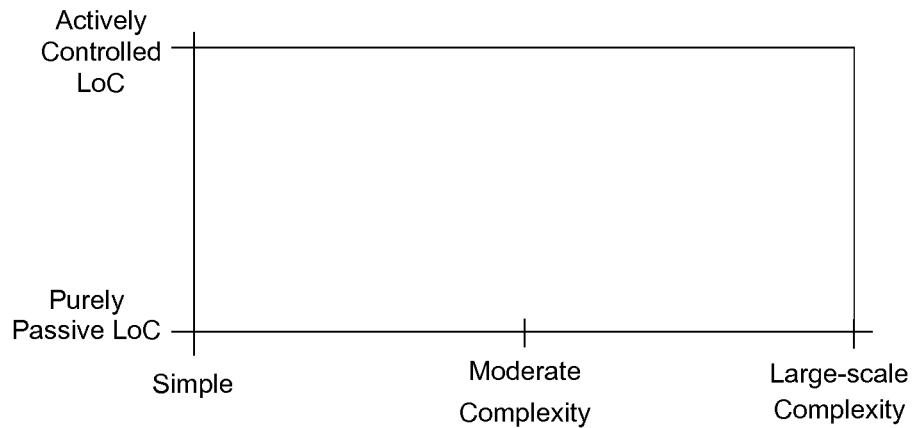
FIG. 1 shows an exemplary two-dimensional attribute space (two-attribute demographic landscape) for LoC devices.

FIG. 1 shows an exemplary two-dimensional attribute landscape that may be used to demographically characterize LoC devices. One attribute of this attribute space relates to systems-level complexity. This attribute is represented by the horizontal axis in the figure. An exemplary metric of systems-level complexity is the total number of primitive elements (by appropriate definition) that define the system. One definition of a primitive element may be a low-level functional component such as a sensor, reactor, pump, valve, and the like.

Currently, very few LoC devices include more than a dozen or so primitive elements. Those with 20 or fewer elements may be viewed as simple, while LoC devices with about 20 to 200 primitive elements may be viewed as having moderate complexity. LoC devices with more than 200 or so primitive elements may be viewed as having large-scale complexity. It is contemplated that future LoC devices may have many hundreds, thousands, tens of thousands, or perhaps even significantly higher numbers of primitive elements.

Another attribute of the two-dimensional demographic attribute space of FIG. 1 relates to whether a LoC device is an operationally passive device or, alternatively, involves active control. The property of active versus passive control is represented by the vertical axis in FIG. 1. Active control may include hardware logic, firmware algorithmic logic, software algorithmic logic, external software control via communication ports, analog feedback control systems, digital feedback control systems, combinations thereof, and the like. Active control may be used for process control, configuration management, and system reconfiguration, among others.

As LoC devices progress from designs of moderate complexity to designs of larger and large-scale complexity, design tools are needed. The needs amplify when active control is added, and yet again when reconfiguration is added. These needed design tools include, among other things, simulation and visualization systems.

Software-controlled configurable and reconfigurable chemical process systems and methods applicable to LoC devices herein may be made on a large enough physical scale that components can be economically manufactured and interconnected by hand. This scaling can includes scales wherein a typical software-controllable functional module may be less than a cubic inch in size, as well as scales wherein a typical software-controllable functional module is large enough to be mounted on standard laboratory stands and lattices and permit hand-customizations.

One interest in the physics of LoC devices arises from the fascinating fluid dynamics, sensor technologies, and clever devices intrinsically relying on micro-millimeter physical scale and nanoliter fluidic volumes. Without fabrication prototyping, research, design, and improvement of features requiring micro-millimeter and nanoliter scale may need to heavily rely on numerical modeling and simulation. However, when prototyping system topologies, process and fluidic, logistics, controller complexity, in situ reaction design, closed-loop sensor-input control system, clearing/cleaning designs, and many other features a physical emulation setup can provide tremendous value. This native value may be further enhanced by including one or more of control, sensing, data recording, and software development infrastructure(s) in a reconfigurable physical emulation setup.

Figure 2A:
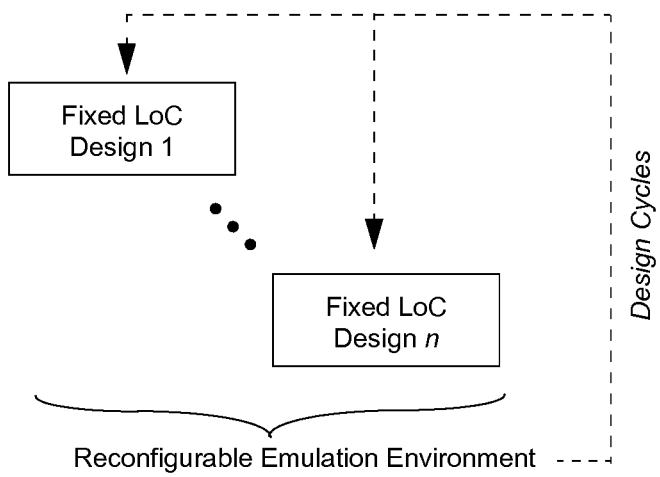
FIG. 2a shows the use of a reconfigurable physical chemical process emulation setup as a tool for developing and conceptual testing of a plurality of fixed LoC systems.

Typically an emulation setup is highly customized around a particular envisioned LoC design. If aspects of the design are changed, the emulation setup typically requires rework, sometimes extensively so. By including software-controllable attributes into the physical chemical process emulating modules themselves and/or by providing at least some degree of software-controllable interconnection, a physical emulation setup can be assembled to provide a range of topological and functional variations that can support a variety of designs and some, much, or all of the evolution of a particular design. FIG. 2a is an example of how a reconfigurable physical emulation setup can span several designs and design variations. In some situations, a reconfigurable physical emulation setup can be used to compare several competing designs. In other situations, a reconfigurable physical emulation setup can be used as a general "workbench" to explore completely unrelated design sketches or side experiments.

Figure 2B:
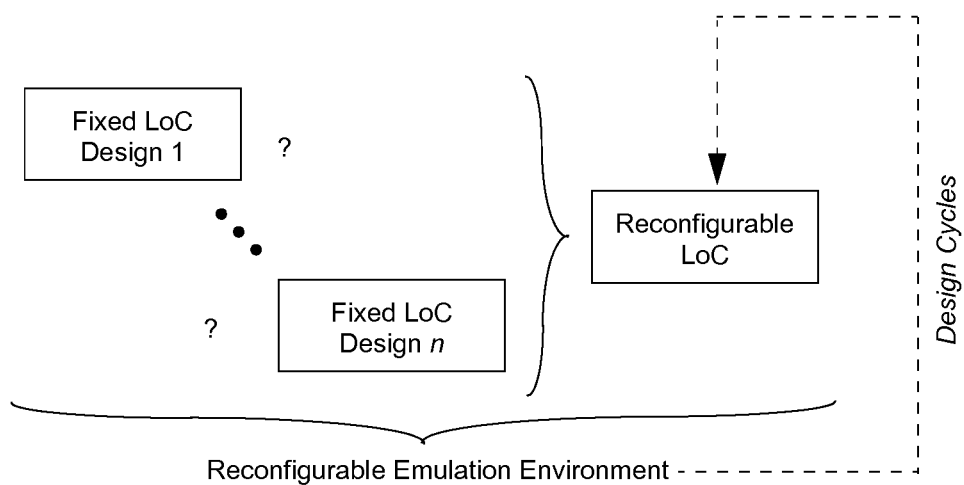
FIG. 2b shows use of a reconfigurable physical chemical process emulation setup as a tool for developing and conceptual testing of reconfigurable LoC systems.

In implementing such reconfigurable physical chemical process emulation setups (which also may be used for other applications, such as laboratory automation in experimental set-ups and laboratory-scale chemical production), many systems and methods for software-controlled configurable and reconfigurable chemical process. Since these systems and methods thus apply to both reconfigurable physical chemical process emulation setups and reconfigurable LoC systems, there is a great and in fact natural utility in employing a reconfigurable physical chemical process emulation setup as a design tool to emulate reconfigurable LoC systems. Thus in addition to the use of a reconfigurable physical chemical process emulation setup as a tool for developing and conceptual testing of fixed designs as shown in FIG. 2a, a reconfigurable physical chemical process emulation setup may be implemented as a tool for developing and conceptual testing of reconfigurable LoC systems, such as that which is shown in FIG. 2b.

Additionally, as reconfigurable LoC systems become available they may in turn be used as components in later-generation larger-scale reconfigurable physical chemical process system.

Reconfigurable Chemical Processing Systems, Reconfigurable LoC, and LoC Commercialization Economics Currently, despite extensive highly-funded basic research, only a very few LoC devices are commercially viable. Most of these, however clever in design, are usually quite simplistic in their complexity. This is largely due to current but long-established research and industry mindset wherein a special dedicated design uniquely serves a particular isolated application area.

This is an unfortunate situation as it creates a network of self-reinforcing self-limiting processes that have long been impeding the industry's effectiveness, value, acceptance, and growth. R&D costs for a full design and subsequent manufacturing costs are very high, typically preventing all but a select few of the simplest devices from reaching manufacture. Further, there is often little opportunity to reuse R&D and manufacturing setups, creating at once both huge opportunity loss and tremendous wasteful industrial process redundancy. The limited manufacturing experience that results diminish chances to improve and refine manufacturing and design techniques, and additionally prevent economies of scale from being leveraged to reduce costs and broaden the possibilities for using LoC technologies.

Figure 3A:
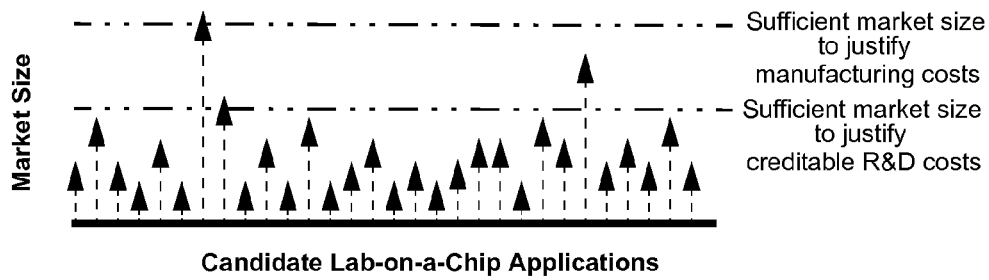
FIG. 3a depicts the situation of potential candidate applications.

FIG. 3a depicts the situation described above. Of the potential candidate applications that could find practical use or otherwise contribute value (represented by the vertical arrows), very few can demonstrate enough market size to justify sizable R&D costs (represented by the three vertical arrows crossing the lower threshold line). Of these, only a very few are even close to being able to demonstrate enough market size to justify the even more sizable manufacturing costs and risks (represented by the single vertical arrow just barely crossing the upper threshold line).

Many of the potential candidate applications (represented by the vertical arrows) in FIG. 3a can be served by associated LoC designs that share a significant number of component features and aspects with one another. Of these, at least one group of LoC designs associated with the selected potential candidate applications can be clustered and fitted with controllable element attributes and controllable routing. The resulting "meta-system" can serve as an archetype design for a reconfigurable LoC system. The archetype design can be further enhanced and perhaps broadened to create a potential reconfigurable LoC product that can serve at least the aggregated markets for potential candidate application in the group.

Figure 3B:
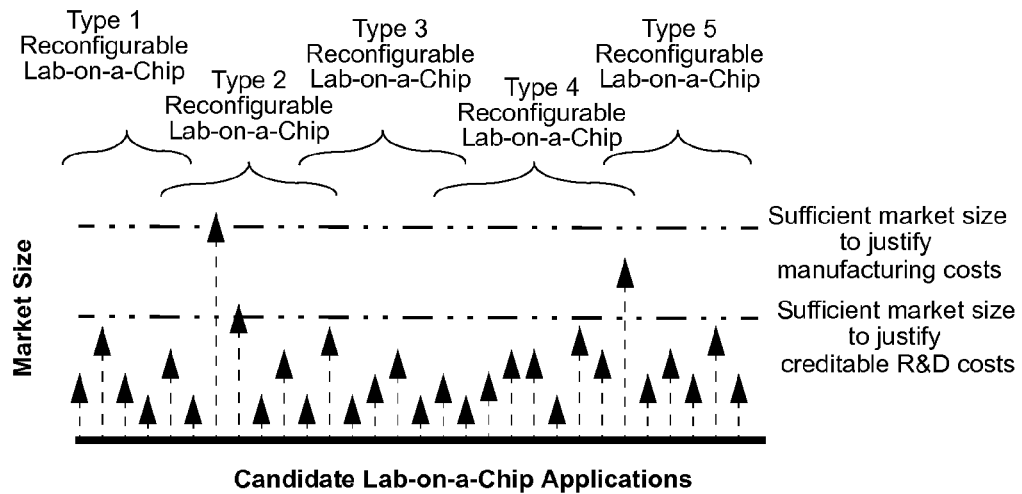
FIG. 3b shows the potential candidate applications of FIG. 3a clustered into five such potential reconfigurable LoC products.

FIG. 3b shows an example of potential candidate applications of FIG. 3a clustered into five such potential reconfigurable LoC products (denoted as Type 1, Type 2, Type 3, Type 4, and Type 5). In many cases, the capabilities of the potential reconfigurable LoC products can be broadened enough so that a few of the potential candidate applications could be served by more than one of the potential reconfigurable LoC products. This overlap is represented in FIG. 3b by the overlapping brackets.

Figure 3C:
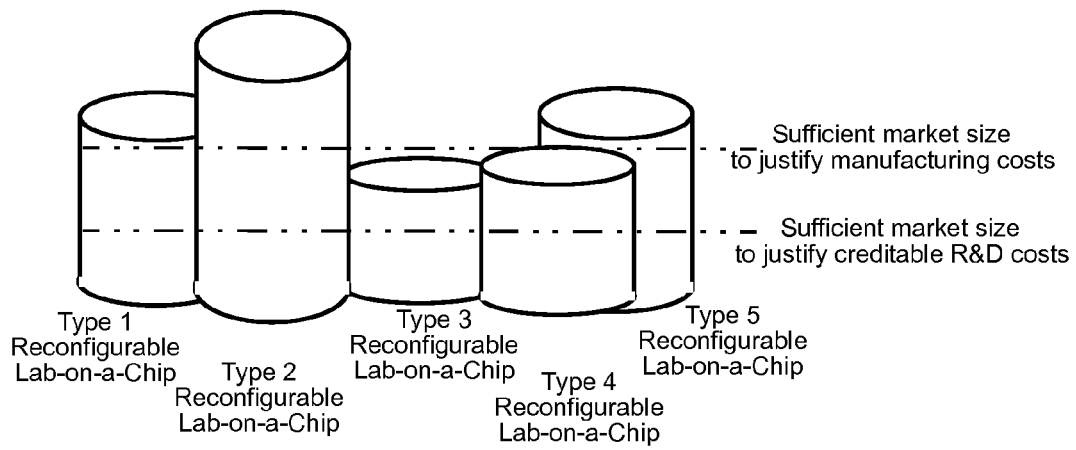
FIG. 3c depicts an example wherein several potential reconfigurable LoC products demonstrate enough potential market to merit both R&D and manufacturing with others defined to aggregate enough market size to merit at least R&D.

Thus a single reconfigurable LoC product, once manufactured, can serve a large number of small-market applications. FIG. 3c depicts this result. For example, at least the Type 1, Type 2, and Type 5 potential reconfigurable LoC products immediately demonstrate sufficiently large potential markets to merit both R&D and manufacturing. In this example, the Type 3 and Type 4 potential reconfigurable LoC products were defined to aggregate at least enough market size to merit R&D, albeit not quite enough market to merit an immediate post R&D manufacturing response.

Figure 3D:
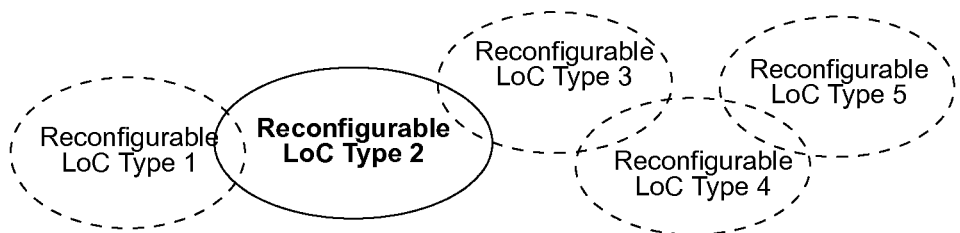
FIGS. 3d-3g depict steps in an exemplary commercialization-enabled scenario demonstrating immense value in pursuing reconfigurable LoC design.
Figure 3E:
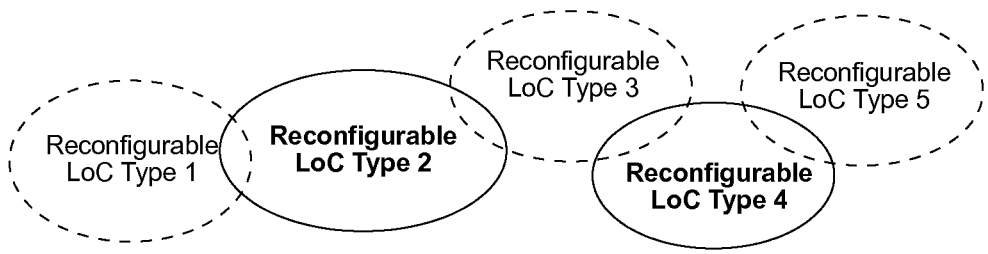

Continuing with the example, various industry and business decisions lead to a first offering of a commercial reconfigurable LoC product—for example of the Type 2 variety—as shown in FIG. 3d. Based on the market response (e.g., good, fair, or bad) and manufacturing lessons learned, desires for shared manufacturing, competitive responses, etc, a second reconfigurable LoC product—for example of the Type 4 variety—is introduced as shown in FIG. 3e. A Type 4 choice may serve as an entirely different market sector that the earlier Type 2 product offering.

Figure 3F:
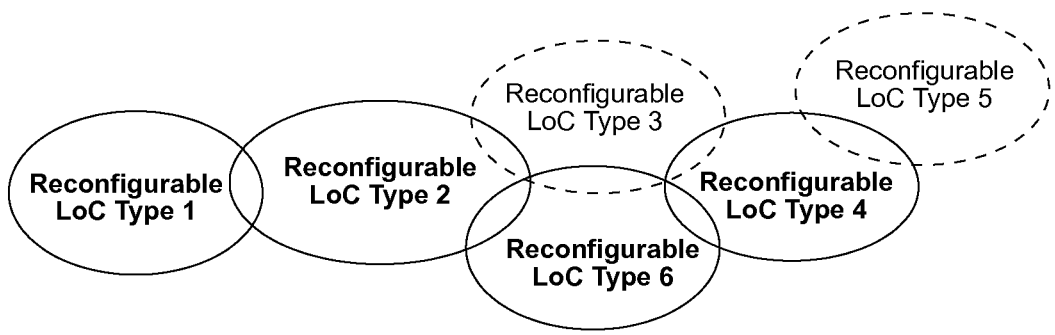

Continuing with the example, there may be market, regulatory, or technical problems that continue to impede Type 3 as originally envisioned, but a competitor may introduce an entirely new Type 6 product that for some applications competes with the now existing Type 2 and Type 4 product offerings. That competitor, another manufacturer entrant, or one of the other manufacturers may also introduce a Type 1 product. This is depicted in FIG. 3f.

Figure 3G:
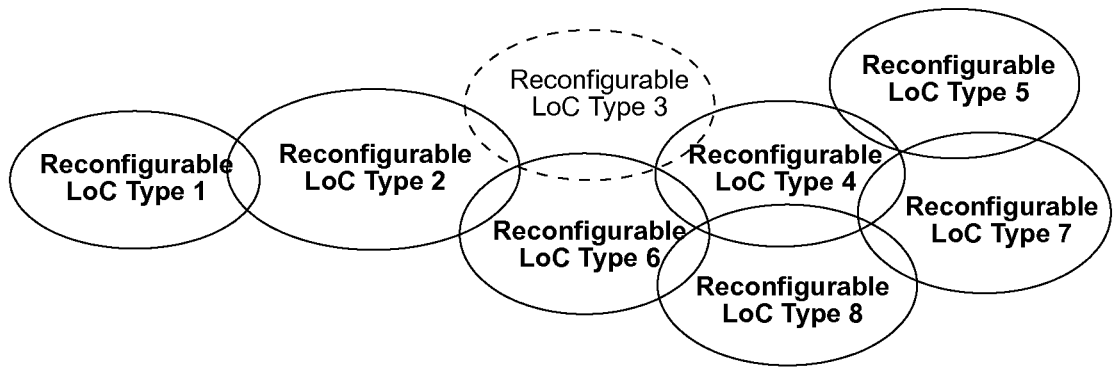

Continuing further with this example, new technology, developing market forces, new applications, and other manufacturer entrants will continue to expand the market. For example, as shown in FIG. 3g, a Type 5 product offering, along with new R&D Type 7 and Type 8 product offerings, are introduced.

Continuing even further with the example the market is now full of LoC solutions for an ever-expanding list of valuable applications, while only a few manufacturing designs were required (for instance, in the example provided here only 7 types of reconfigurable LoC products are manufactured). Further, the mass production encourages a growing skill-base in using these reconfigurable LoC products, putting these 7 reconfigurable LoC in the same role as that of the selection of available microprocessors and embedded controllers in the electronics and computer industry—that is, once available and understood, they become tools for many additional unforeseen applications by a great many more customers.

The exemplary scenario of FIGS. 3b-3g demonstrates the immense value in pursuing reconfigurable LoC design. First, the aggregation of application fractured markets made possible by properly designed reconfigurable LoC products breaks the long-standing stalemate depicted in FIG. 3a. Second, not only does a reconfigurable physical chemical process emulation setup provide a development environment with the value spelled out in the discussion of FIG. 2a, but additionally the reconfigurable physical chemical process emulation setup and reconfigurable LoC both inform and cross-enable one another. This rationale provides even more reasons for producing commercial component products, and entire systems, for reconfigurable physical chemical process emulation.

Configurable and Reconfigurable LoC, Clearing and Cleaning, and Further LoC Classifications Attention is now directed to classification remarks concern matters of distinguishing initial configuration, modal operation, and reconfiguration:

In many situations and applications, one or more instances of one or more setup actions may be enacted prior to the operation of the reconfigurable LoC or reconfigurable chemical process emulation system. This enactment establishes an initial configuration of the LoC or emulation system.

In many situations and applications, limited valve operation and other topological actions may be enacted during operation of the reconfigurable LoC or reconfigurable chemical process emulation system. These enactments may be viewed as modal operation within a previously established initial configuration.

In some situations and applications, significant variations or fundamental structural changes are enacted; these may be viewed as a reconfiguration of the associated larger system.

In some embodiments and applications, portions of a reconfigurable LoC or reconfigurable chemical process emulation system may be designated for single substance-type use, single-purpose use, or even single-event use. In other embodiments and applications, at least portions of a reconfigurable LoC or reconfigurable chemical process emulation system may provide for some form of clearing and cleaning of at least some portions the reconfigurable LoC between at least some operations to allow buses, valves, and in many cases connected devices to be reused with limited contamination. These clearing and cleaning operations can deliver several features including, for example, any or all of the following:

Permit multiple reuse of the LoC within a larger system (for example a mass-produced consumer-level food-toxin tester);

Removal of toxins prior to recycling or disposal;

Recovery of valuable reagents prior to recycling or disposal.

Figure 4:
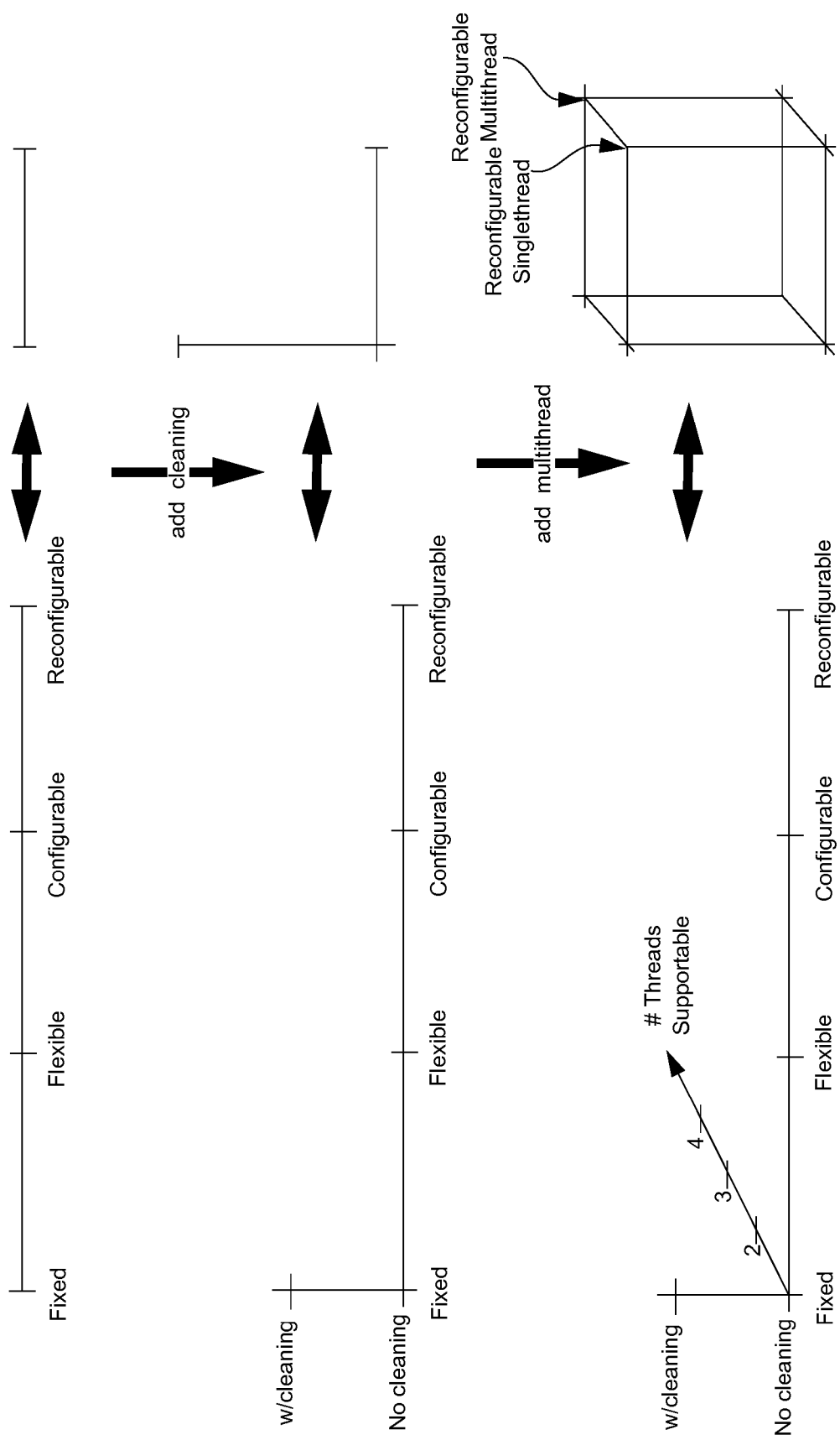
FIG. 4 shows the construction of another attribute space relevant to the inclusion of reconfigurable LoC devices and emulation systems emulating LoC devices.

As previously discussed, FIG. 1 provided an exemplary two-dimensional attribute space for demographically defining LoC devices. The two attributes defining the two-dimensional attribute space are metrics of complexity and of passivity versus active control employed by the LoC. In view of the additional considerations raised thus far, FIG. 4 shows the construction of another attribute space relevant to the inclusion of reconfigurable LoC devices and emulation systems emulating LoC devices. In this example of FIG. 4:

The first attribute is an index relating to whether an LoC device or LoC emulation system has a fixed configuration, some degree of primitive flexibility in its configuration, a software or other electrical "configurable" (i.e., controllable) configuration, or a reconfigurable configuration that may be changed within the actual operation time of the system.

An added second attribute pertaining to whether the LoC device or LoC emulation system includes internal clearing and cleaning capabilities.

An added third attribute pertaining to the number of simultaneous independent processing "threads" or activities that can be simultaneously supported. This is analogous to the number of simultaneous real-time control threads that may be supported by a real-time microprocessor or Digital Signal Processing (DSP) chip.

Simulation, Emulation, and Control Environment

Figure 5:
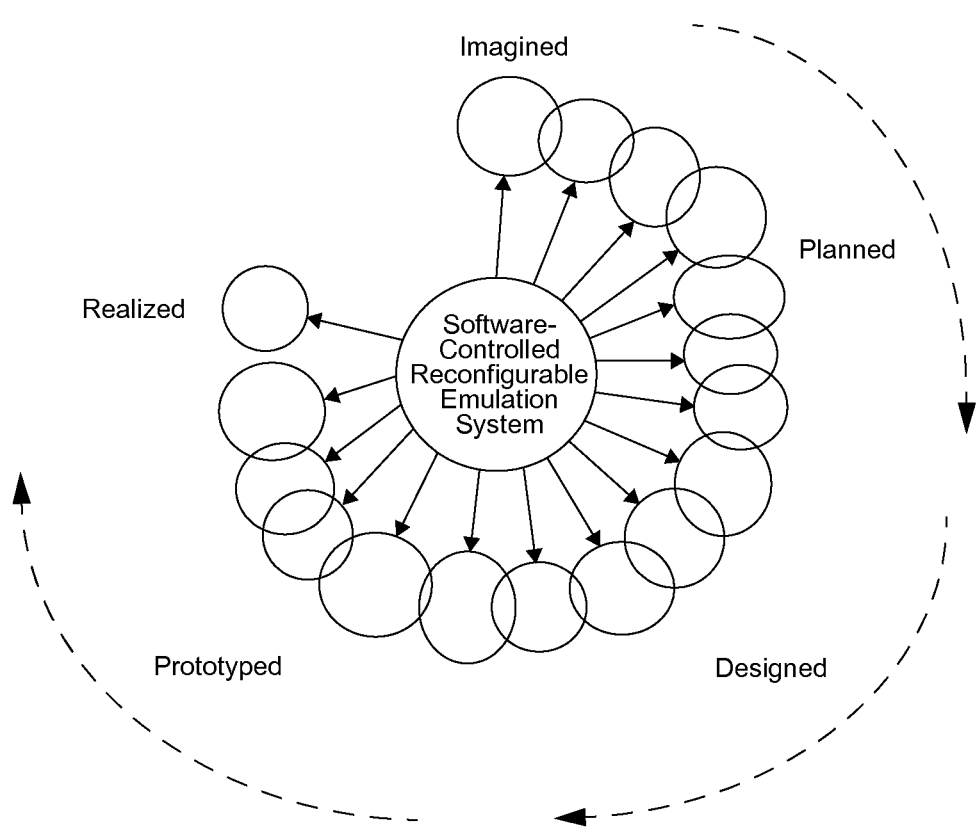
FIG. 5 shows a software-controlled reconfigurable LoC emulation system that can be used to emulate a wide range of differing imagined, planned, designed, prototyped, and/or realized LoC devices.

FIG. 5 shows a software-controlled reconfigurable LoC emulation system that can be used to emulate a wide range of differing imagined, planned, designed, prototyped, and/or realized LoC devices. As such, the reconfigurable LoC emulation system can potentially provide value throughout virtually the entire research, development, design, prototype, and pre-manufacturing cycle of a LoC or reconfigurable LoC product.

Further value can result by integrating a software-controlled reconfigurable LoC emulation system together with simulation, software development, visualization, and other design tools in a common environment. Exemplary methods and systems for this which are applicable to the present disclosure are described in provisional patent application entitled "Software Systems for Development, Control, Programming, Simulation, and Emulation of Fixed and Reconfigurable Lab-on-a-Chip Devices," Ser. No. 61/005,460, filed Dec. 4, 2007, and the patent application entitled "Software Systems for Development, Control, Programming, Simulation, and Emulation of Fixed and Reconfigurable Lab-on-a-Chip Devices" filed concurrently herewith (Ser. No. 12/328, 726) and which also claims benefit of priority of application Ser. No. 61/005,460. Here, a few examples are provided that may be advantageous in various embodiments, implementations, and applications.

Figure 6A:
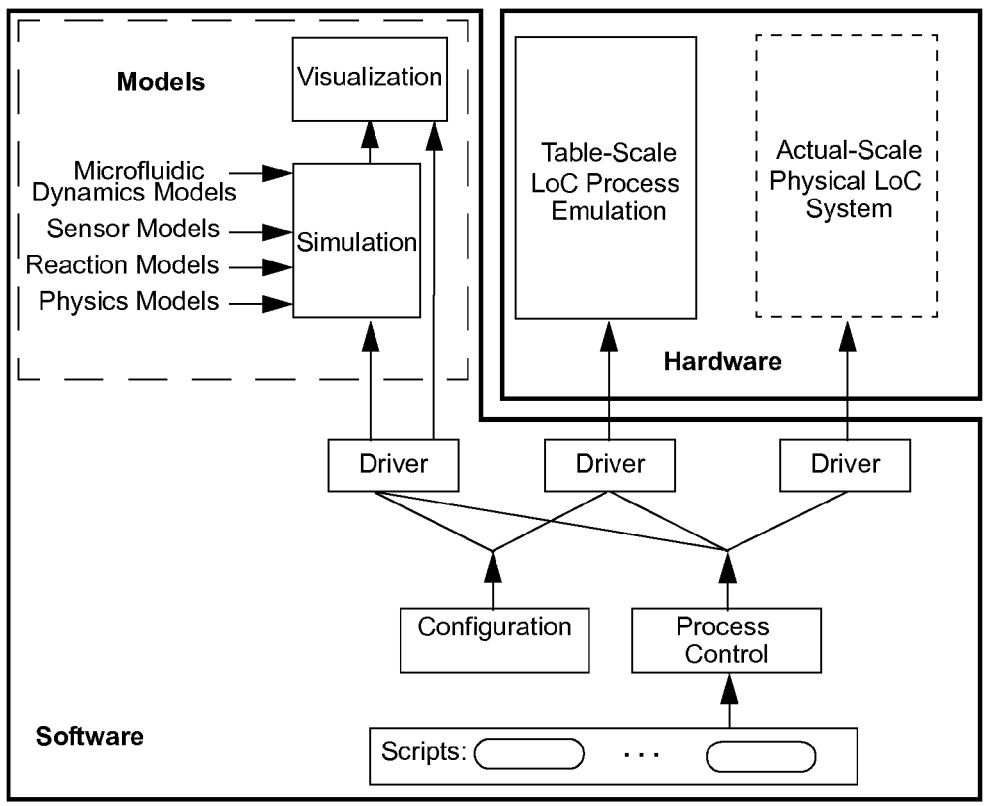
FIG. 6a shows a global view of an integrated system for simulation, emulation, and in some applications direct control of a fixed-design LoC device from one or more common scripts and/or files.

FIG. 6a shows a global view of an embodiment of an integrated system. In this embodiment the actual LoC device under development, study, or operation does not have configuration or reconfiguration abilities. The integrated system may be used for progressive and/or interspersed simulation, emulation, and, where applicable, direct control of an LoC device from one or more common scripts and/or files.

In FIG. 6a, the same scripts and/or files may be used to operate a process control element in communication with various target-specific drivers. In this example, one such driver is associated with a numerical LoC modeling system having a simulation component and a visualization component in addition to other detail numerical models. Another such driver is associated with a "table-scale" or other LoC emulation system. Alternatively or additionally, another driver is associated with an actual LoC device should it exist or be available. Other approaches are possible as is clear to one skilled in the art.

Additionally, the embodiment of FIG. 6a may be implemented with both the numerical LoC modeling system and the LoC emulation system as being configurable or reconfigurable. The same or similar configuration scripts and/or files and/or other techniques may be used to configure the numerical LoC modeling system and the LoC emulation system.

Figure 6B:
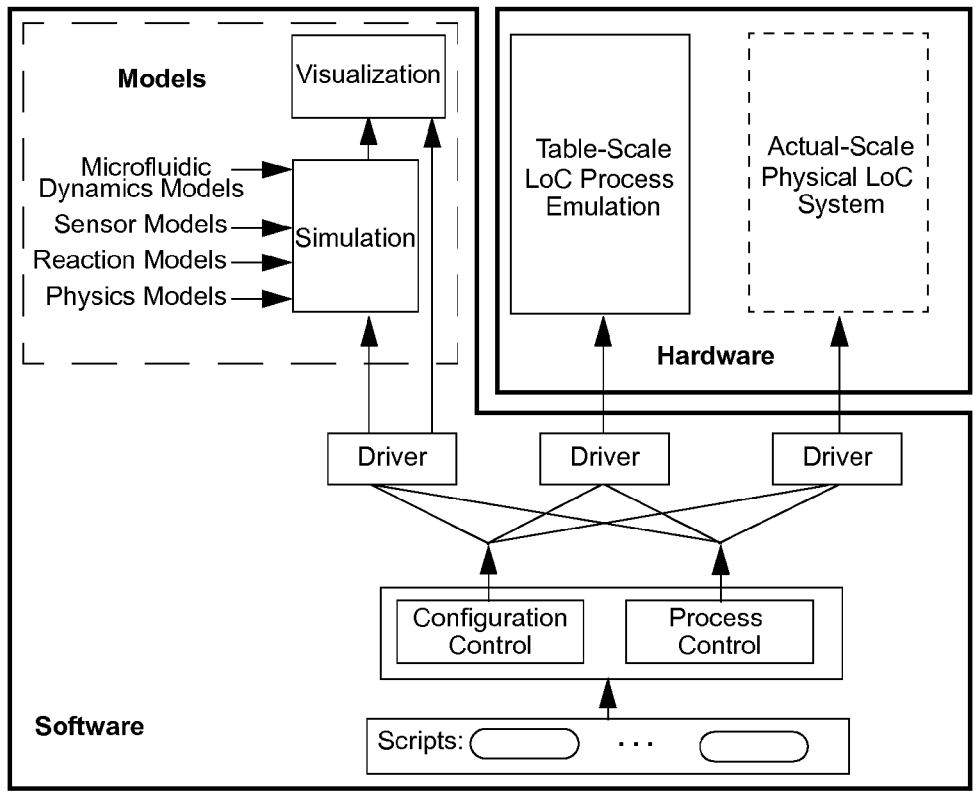
FIG. 6b shows a global view of an integrated system for simulation, emulation, and in some applications direct control of a configurable or reconfigurable LoC device from one or more common scripts and/or files.

FIG. 6b shows an exemplary adaptation of the arrangement of FIG. 6a wherein the actual LoC device under development, study, or operation has configuration or reconfiguration abilities. In this figure, common configuration scripts and/or files and/or other techniques may be used to configure the numerical LoC modeling system, the LoC emulation system, and the LoC device itself should it exist and be available. Further, it may be useful to integrate configuration control in with process control as shown in FIG. 6b. In this way scripts and/or files may commingle configuration commands and process commands.

Exemplary Software Architectures

It is understood that many software architectures can be employed for actively controlled LoCs, reconfigurable LoCs, and LoC emulation systems, and more general reconfigurable chemical processing systems. Exemplary methods and systems for these software architectures that may be implemented by the various embodiments disclosed herein are described in provisional patent application entitled "Software Systems for Development, Control, Programming, Simulation, and Emulation of Fixed and Reconfigurable Lab-on-a-Chip Devices," Ser. No. 61/005,460, filed Dec. 4, 2007, and the patent application entitled "Software Systems for Development, Control, Programming, Simulation, and Emulation of Fixed and Reconfigurable Lab-on-a-Chip Devices" filed concurrently herewith (Ser. No. 12/328,726) and which also claims benefit of priority of application Ser. No. 61/005,460.

Figure 7A:
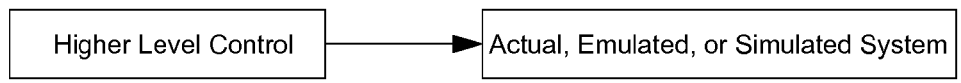
FIG. 7a shows a high-level view of an exemplary software architecture in which a higher-level control system controls any one or more of a target actual, emulated, or simulated system.

FIG. 7a shows a high-level view of an exemplary software architecture wherein a higher-level control system controls any one or more of a target actual (physical), emulated (physical) or simulated (numerical model) system. The target physical or simulated system may include one or more of a LoC device, a software-controlled LoC emulation system, and a numerical simulation of some or all components of a LoC device.

Figure 7B:
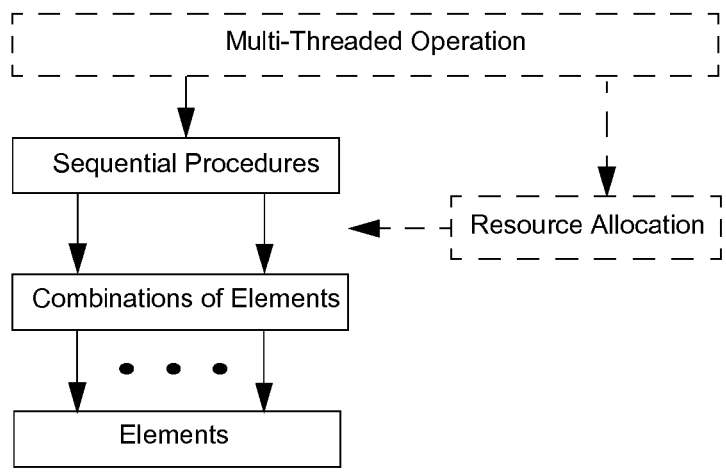
FIG. 7b shows an exemplary control hierarchy of such an exemplary software architecture.

FIG. 7b shows an exemplary control hierarchy of such software architecture. At the lowest level are private elements such as valves, heaters, motors, electrodes, optical devices, and the like. At the next level are combinations of these that may be addressed together to invoke a particular mode or posture of operation. At the next level are sequences of these that may be used to invoke and/or control a temporally process or other more complex operation.

Figure 7C:
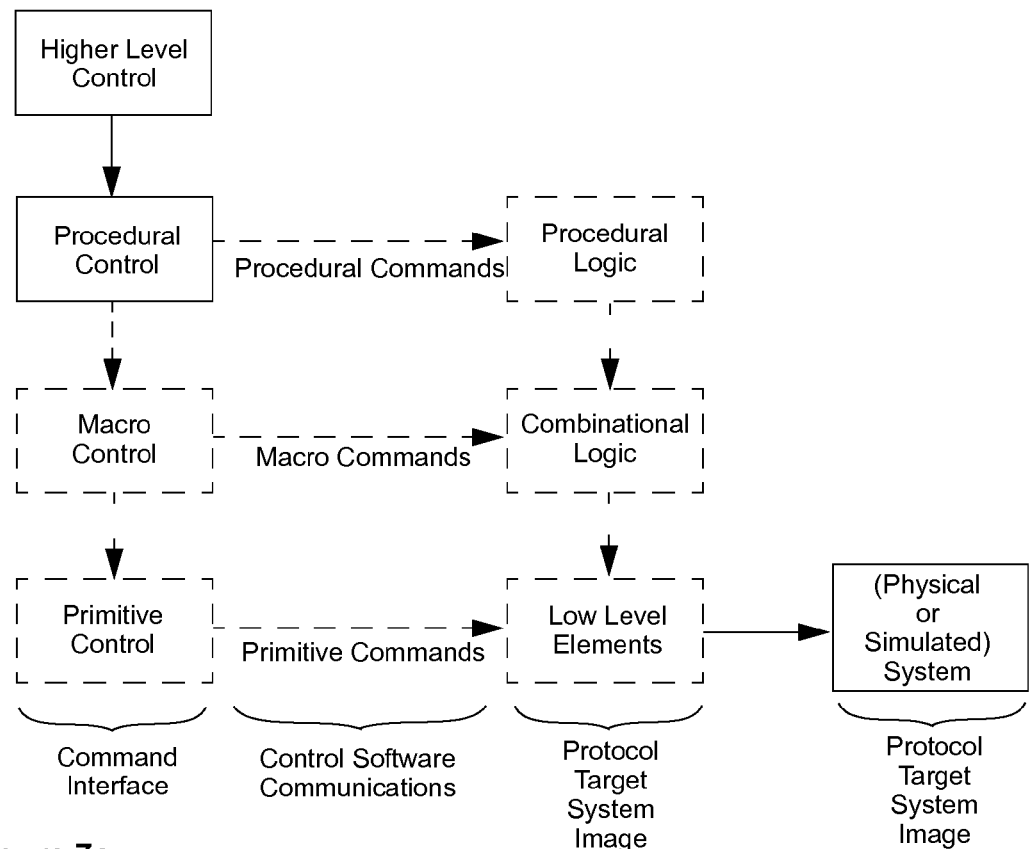
FIG. 7c shows an exemplary transactional organization for an exemplary hierarchy of control.

FIG. 7c shows an exemplary transactional organization for an exemplary hierarchy of control. This hierarchy of control may include a control system or command interface (left column), an exemplary hierarchy of control that may include an LoC device, LoC emulation system, LoC simulation, etc. (right column) which ultimately controls the target system (LoC device, emulation, simulation, etc.), and an exemplary hierarchy of commands that may be used to communicate between the two hierarchies of control. At the lowest level, individual low level elements may be directly controlled. At the next level, combinations of elements and simple associated subsystems may be directly controlled. At the next level higher, procedures may be specified. A potential advantage may be achieved if a common language and/or protocol can be used for each level of the hierarchy of commands regardless of the target. This common language and/or protocol may be structures in subsets, libraries, function calls, etc. and may optionally or advantageously be extensible and/or open.

General Overview of Exemplary Chemical Process Modules for LoC Emulation and Laboratory Automation One skilled in art will appreciate that the systems and methods described in the examples below, for example, are exemplary yet readily extendable to a wide range of variations and adaptations. Such wide-ranging variations and adaptations are fully anticipated by the present disclosure.

In various embodiments, an exemplary LoC emulation system may include combinations of:

Electrically-controlled miniature fluid and gas (gating and routing) valves;
Small chemical reactors with thermal control;
Electrical output sensing elements for various physical quantities;
Interconnecting tubing;
Electrically-controlled (low DC voltage) fluid and gas transport;
Control interface electronics;
Sensor interface electronics; and
Communications electronics;

The above elements and others may be organized into modules that may be designed to handle fluids, gasses, and mixed-media/vapors. These modules may include local control, power management, status indication, and communications electronics.

In one approach, clocked "two-wire" bi-directional serial communications (such as the $I^2C$ "Inter-Integrated Circuit" protocol) may be used. Other implementations may employ self-clocking "one-wire" bi-directional serial communications, parallel communication buses, etc. In various embodiments, status indication for a given module or group of modules may include LEDs, character displays, graphics displays, etc. In some situations, it may be advantageous to employ commercial products (such as those manufactured by Matrix Orbital and others) that combine character/graphics displays, communications electronics, and on/off electrical outputs and inputs. In other situations, widely available communications chips, such as those made by Analog Devices and Dallas Semiconductor, providing addressable parallel latched data ports, DAC, ADC, temperature sensing, and other functions may be used as a principle component of communications electronics. In yet other implementation, simple addressable latch logic chips or discrete circuitry may be used.

One skilled in the art will appreciate that physical support and interconnection may be handled in a variety of ways. In one embodiment, modules may be in the physical form of a cuboid of various regulated sizes; these cuboid modules may plug into a backplane system and/or may include a free-form "patch panel" of electrical connectors and fluidic/gas ports.

In another embodiment, modules may be realized on microscope slides with side-mounted electrical and fluidic/gas port connections that "plug" into a backplane.

In another embodiment, laboratory lattice clamps may be used for support, electrical connectors for power and signals, and fluidic/gas connectors to provide well-defined ports for the connection of one or more types of tubing. An example of this is provided in FIG. 8a.

Figure 8A:
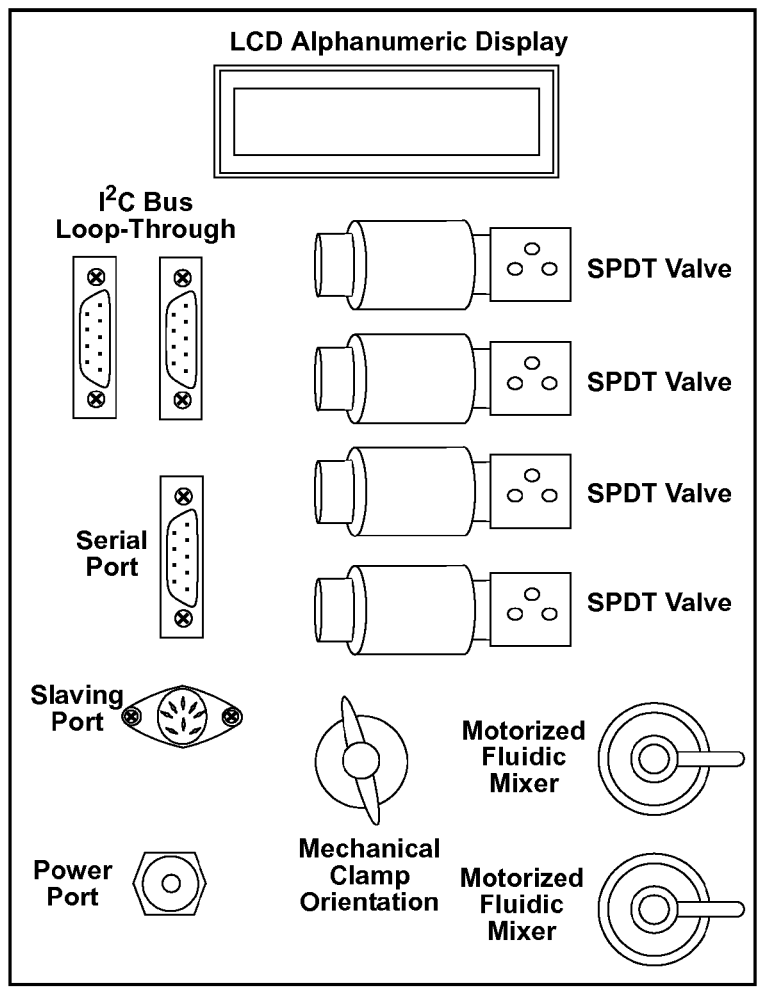
FIG. 8a depicts an exemplary laboratory lattice-scale implementation of an exemplary module as provided for by an embodiment of the invention.

In laboratory lattice-scale implementations such as those provided in FIG. 8a, it may be advantageous to provide multiple forms of input control. For example, the example provided in FIG. 8a may be controlled in any of three ways:

A serial port, useful for isolated operation by a laptop computer in a small-scale laboratory automation application;

An I²C loop-through port, useful for bus communications in multiple-module setups as typically would be encountered in an emulation system or large-scale laboratory automation application;

A contact-closure port; useful for simple testing or operation by simple switches or relay contacts.

Of these, the contact-closure port may often be unused in sophisticated setups, but with proper electrical design the contact closure port can be used for slaving arrangements with tightly-coordinated subordinate modules, for example as may be used with venting and pressure equalization arrangements as described later.

The contact closure port may be entirely space-division (i.e., a separate electrical circuit at the port for each controlled element) or may advantageously employ a more sophisticated protocol to limit the number of wires involved. Further, this protocol can be incorporated into control logic that both decodes the protocol and translates it into meaningful operations within the module while preventing harmful or meaningless combinations of element actuations. In the examples provided, the following exemplary protocol is employed:

A "flow" command (denoted as "f") directs chemical substances to flow through a valve complex. Flow occurs only when "f" takes on a specific binary state (e.g., when connected to ground);

A "clearing/cleaning" command directs chemical substances to flow through a valve complex. Clearing and cleaning occurs only when "c" takes on a specific binary state (e.g., when connected to ground);

An idle condition is invoked with neither "f" nor "c" is active (i.e., not grounded or pulled to a logical "high" level);

A "no-op" is involved should both the "f" nor "c" be active simultaneously.

A binary "type" word (denoted as "t" with bits "$t_0$", "$t_1$", etc. as needed) is used to select the type of chemical substances that is to flow through the valve complex or the input/output port to be employed;

A binary "void" word (denoted as "φ" with bits "$\phi_0$", "$\phi_1$", etc. as needed) is used to select the type of clearing and cleaning operation to be invoked.

Other protocol approaches are possible of course as is clear to one skilled in the art.

In one embodiment, on/off and binary-word control signals can be provided a parallel I/O communications chip such as the Phillips I²C PCF8584 or Dallas "1-wire" DS2406, etc. Conversions between I²C and 1-wire can be provided by chips such as Broadcast Equipment BL233B or Dallas DS2482. The Broadcast Equipment BL233B also implements conversions among RS-232 and the aforementioned I²C and 1-wire protocols.

In laboratory lattice-scale implementations, for example, any of a number of Matrix Orbital Display products such as the LK, VK, and GLK series simultaneously provide I²C and RS-232 communications, binary inputs (keypad matrix format) and open collector outputs ("general purpose controllers") in addition to alphanumeric display. The I²C port may be interfaced with chips such as Broadcast Equipment BL233B or Dallas DS2482 to provide interfacing to the 1-wire protocol.

Figure 8B:
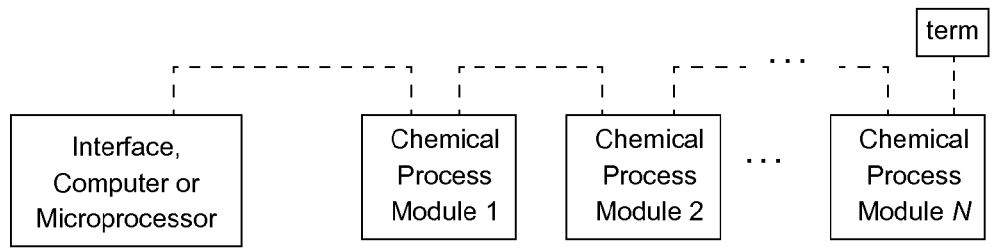
FIG. 8b depicts an exemplary loop-through implementation of communications bus connecting exemplary modules with a controlling computer or processor as provided for by an embodiment of the invention.
Figure 8C:
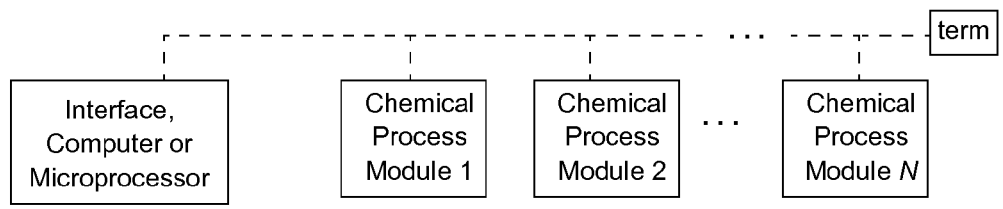
FIG. 8c depicts an exemplary backplane implementation of communications bus connecting exemplary modules with a controlling computer or processor as provided for by an embodiment of the invention.

FIG. 8b depicts an exemplary loop-through implementation of a communications bus connecting exemplary modules with an interface, computer, or micro-processor according to an embodiment of the invention. Typically the bus is daisy-chained as depicted by the dashed lines in FIG. 8b. The use of a pair of connectors on each module, connected between modules via a jumper patch cable, enforces this approach. The otherwise unused connector of this connector pair of the module at the end of the daisy-chain is provided with an electrical bus termination element. One reason for this element is to prevent reflections that would corrupt high-speed communications. The electrical bus termination element may be implemented as a plug-in that mates with the otherwise unused connector (in place of the jumper patch cable), or may be implemented as an auto-sensing switched termination. In other embodiments, such as that depicted in FIG. 8c, a path on an electrical backplane is used to provide the communications bus, and the electrical backplane internally provides the electrical bus termination element.

Typically each of the communications elements sharing the I²C, 1-wire, or other bus is set to a different unique bus address. Each module may include a range of addresses assigned to it. Typically addresses are set by wiring specific pins to selected binary voltage levels; this may be handled by DIP switches, hard-wiring, or the use of other techniques. In some embodiments, such as in implementations using the Matrix Orbital products, the address may be downloaded by a configuring or controlling computer or processor.

In other (for example, physically smaller) embodiments, the "open-collector"/"open-drain" parallel ports of the Phillips I²C PCF8584 chip, output from individual Dallas "1-wire" DS2406 chips, etc. may be connected the digital control inputs directed to the aforementioned contact-closure port (for example in the exemplary circuits provided in FIGS. 9b, 10b, 11b, 12b, 13b, 14b, 15b, and 16b to follow) and/or replacing the Matrix Orbital "GPO" interface in the exemplary circuits provided in FIGS. 17b, 18b, 19, 22 and 23 to follow.

Figure 23:
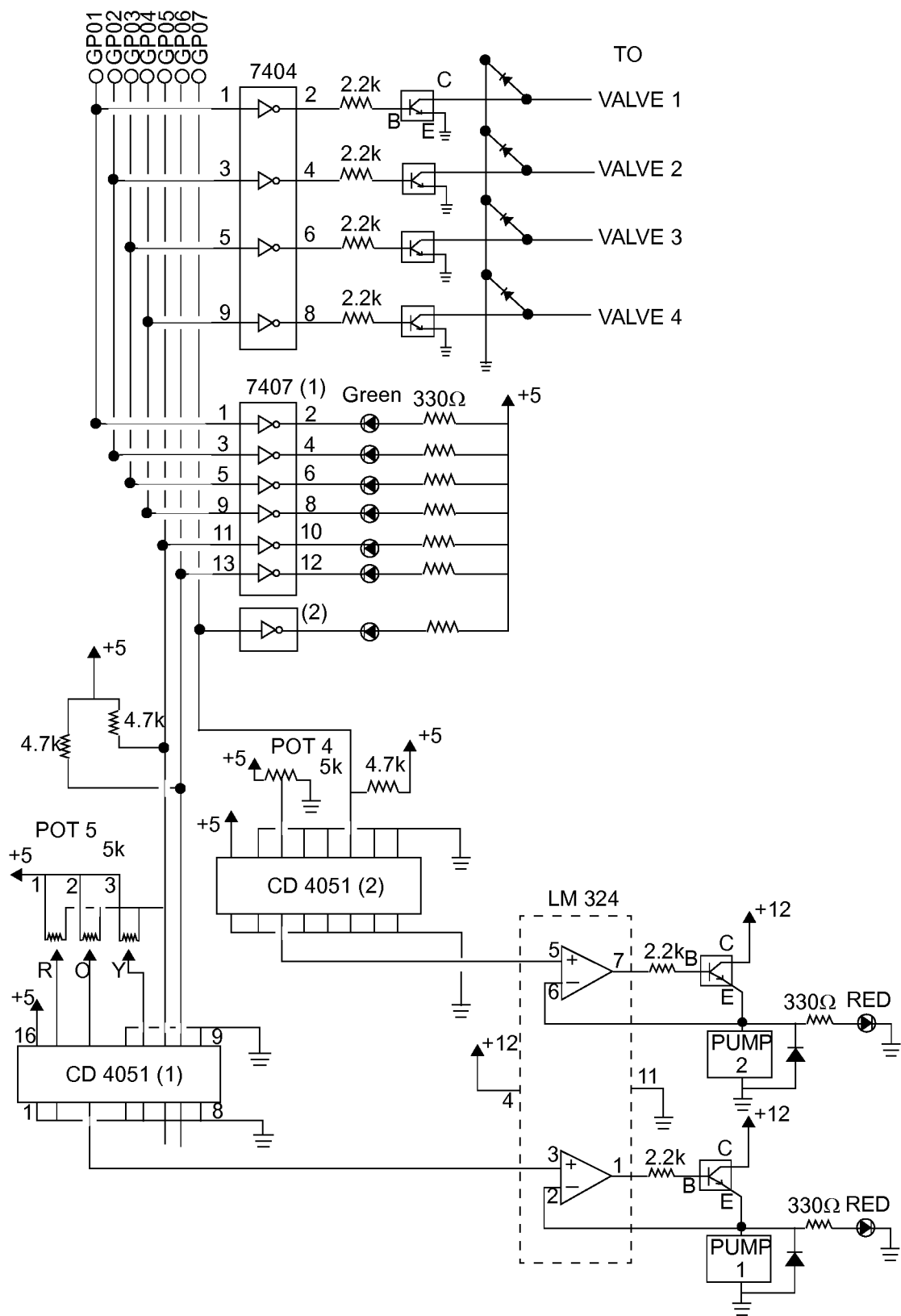
FIG. 23 depicts exemplary multichannel electronics.

One skilled in the art will appreciate that variable analog voltage or current outputs can also be provided for the control of variable-speed pump motors, heating elements, electro-chemistry elements, etc. Referring ahead to FIG. 23, an exemplary multichannel electronics design is shown providing not only switched outputs for valves but also multichannel analog voltage outputs, each selecting from a plurality of hand-adjustable voltage settings and each providing adequate drive current and inductive load protection to drive variable-speed motorized diaphragm pumps, small heating elements, etc. For fully-adjustable analog voltage control via digital communications ports, a D/A converter may be employed. Many voltage I²C ADC chips are available (such as Maxim MAX1069, MAX1169, MAX1236, etc., Texas Instruments DAC6573, etc.), and at least one self-contained 1-wire ADC current chip (such as Dallas DS4402 DS4404) is available.

Additionally, variable analog voltage inputs may be provided, particularly for sensor interfacing. These are readily provided by A/D converters. There are a number of voltage ADC chips with built-in communications features (such as Maxim MAX1069, MAX1169, MAX1236, etc. for I²C, DS2450 for "1-wire"), and some have built-in temperature sensors (such as I²C AD7992 and "1-wire" DS1920). In some embodiments, small-profile (surface mount) packages of these ADCs with integrated temperature sensors (such as I²C AD7992 and "1-wire" DS1920) may be appropriately encapsulated and used directly as a contact and/or immersed temperature sensor.

Other approaches are possible using, for example, the many digital, analog, communications, and computation features provided by PIC, 81xx-series, and ARM microcontrollers or various microprocessors and mixed signal controllers.

Figure 9A:
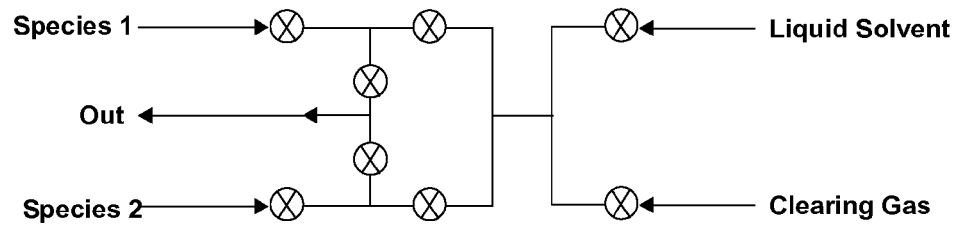
FIG. 9a shows an exemplary fluidic/gas path implementation of a 2:1 input 8-valve complex.
Figure 9B:
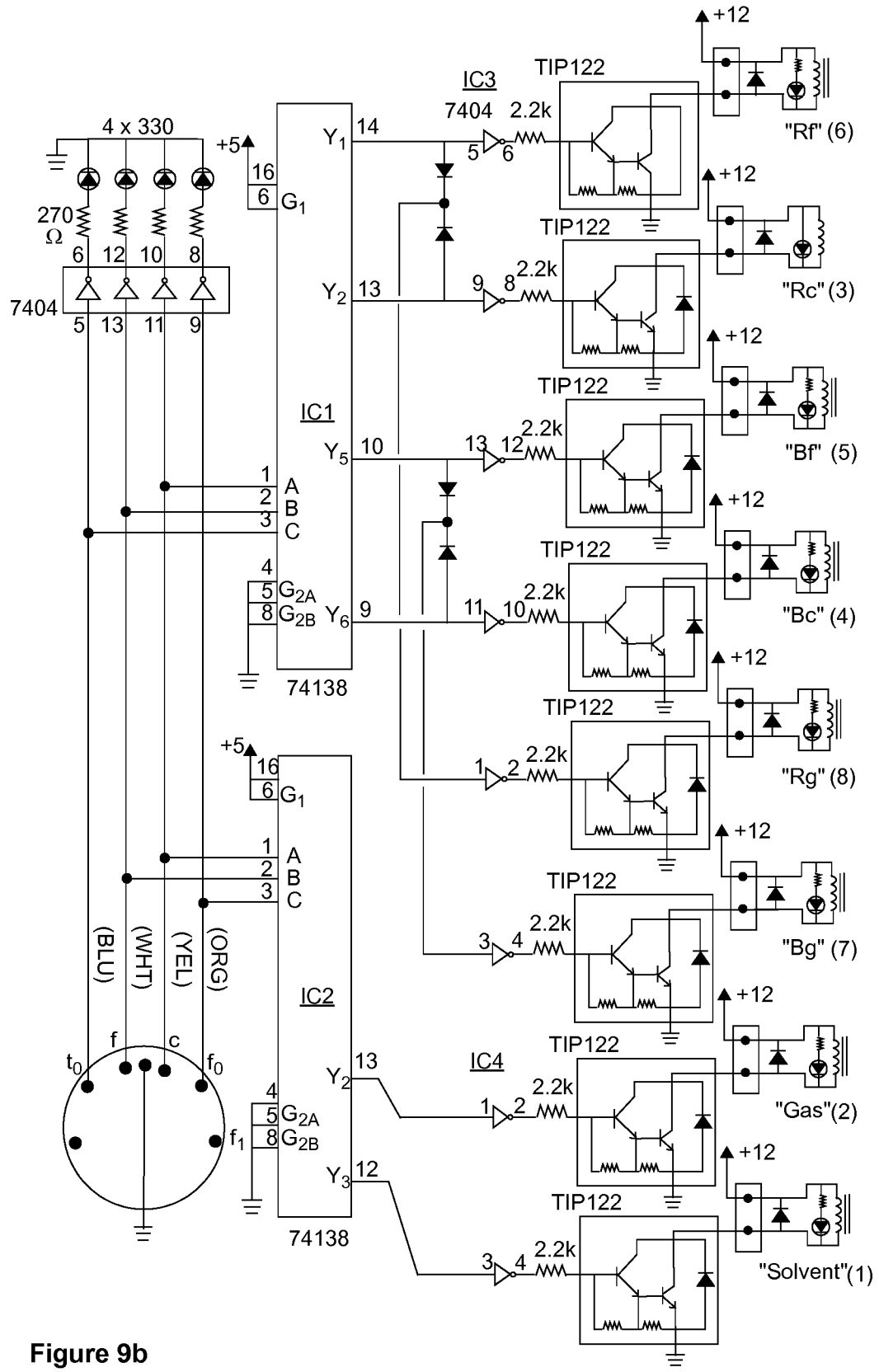
FIG. 9b shows an exemplary electronic implementation of a 2:1 input 8-valve complex.

Exemplary Reconfigurable Fluidic/Gas Routing Systems with Clearing and Cleaning Provisions Employing On/Off Valves FIG. 9a shows an exemplary fluidic/gas path implementation of a 2:1 input 8-valve complex. This realization has provisions for clearing and drying with a clearing gas and cleaning with a liquid solvent. FIG. 9b shows an exemplary electronic implementation of the 8-Valve Complex. Various colored LEDs may be provided, as shown in this figure, to indicate valve flow status. Other flow management and electrical approaches are possible.

Figure 10A:
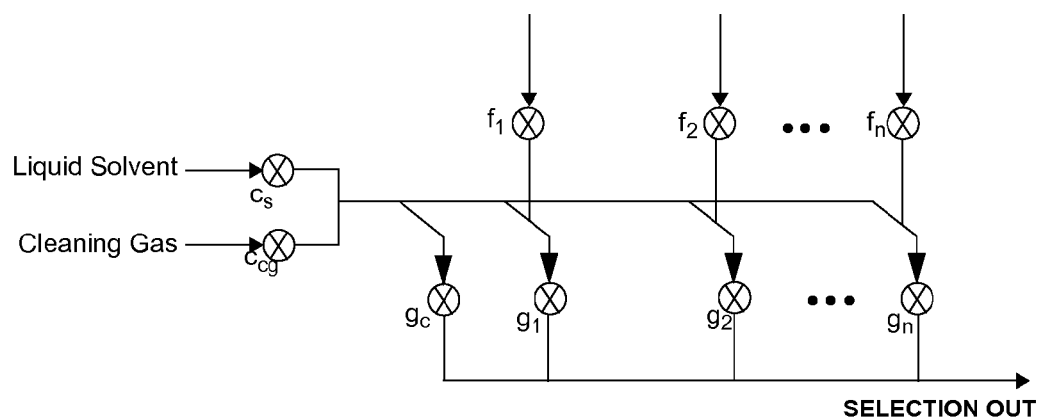
FIG. 10a shows an exemplary fluidic path implementation of a n:1 input 11-valve complex.
Figure 10B:
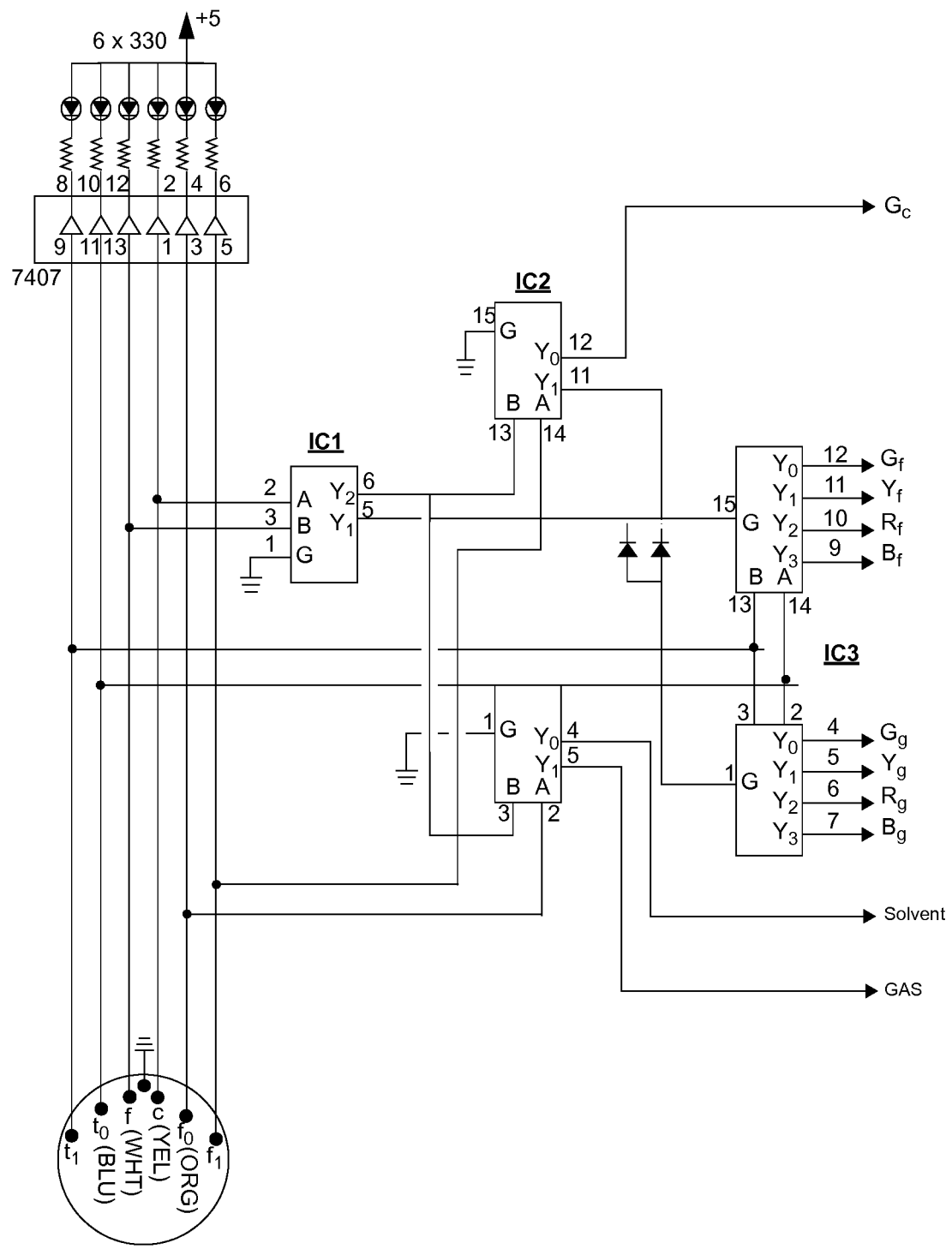
Figure 10C:
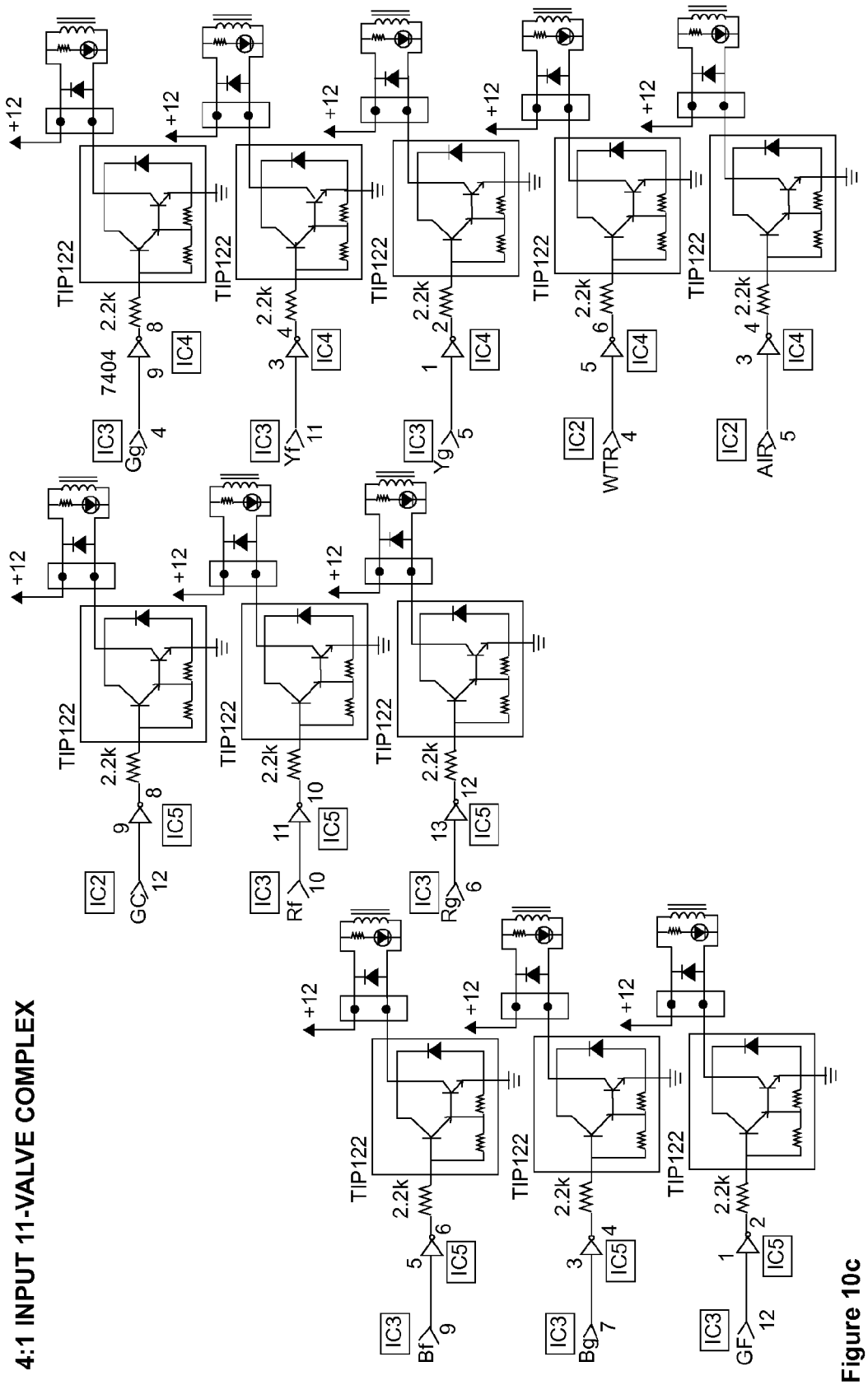
Figure 11A:
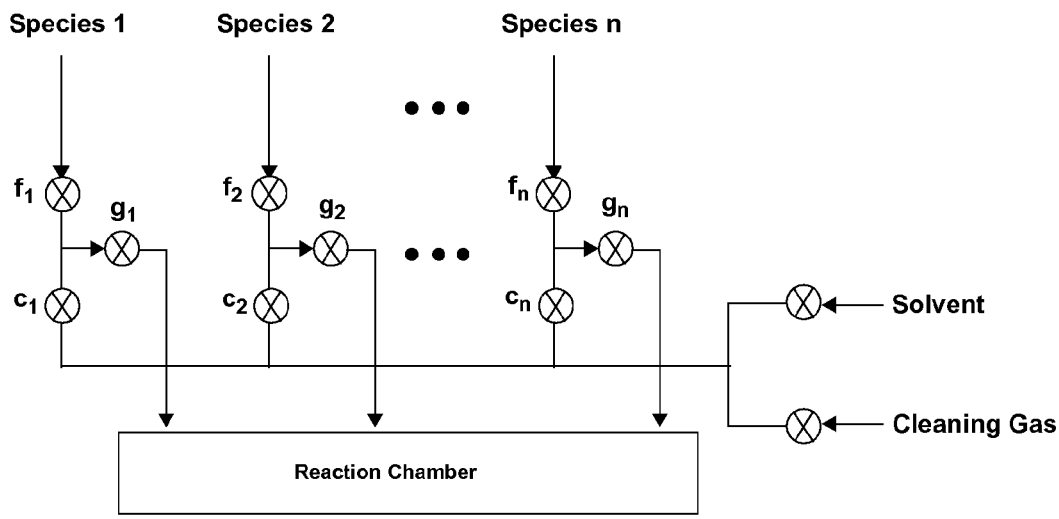
FIG. 11a shows an exemplary fluidic path implementation of a n:n input valve complex for multiport reaction chambers.
Figure 11B:
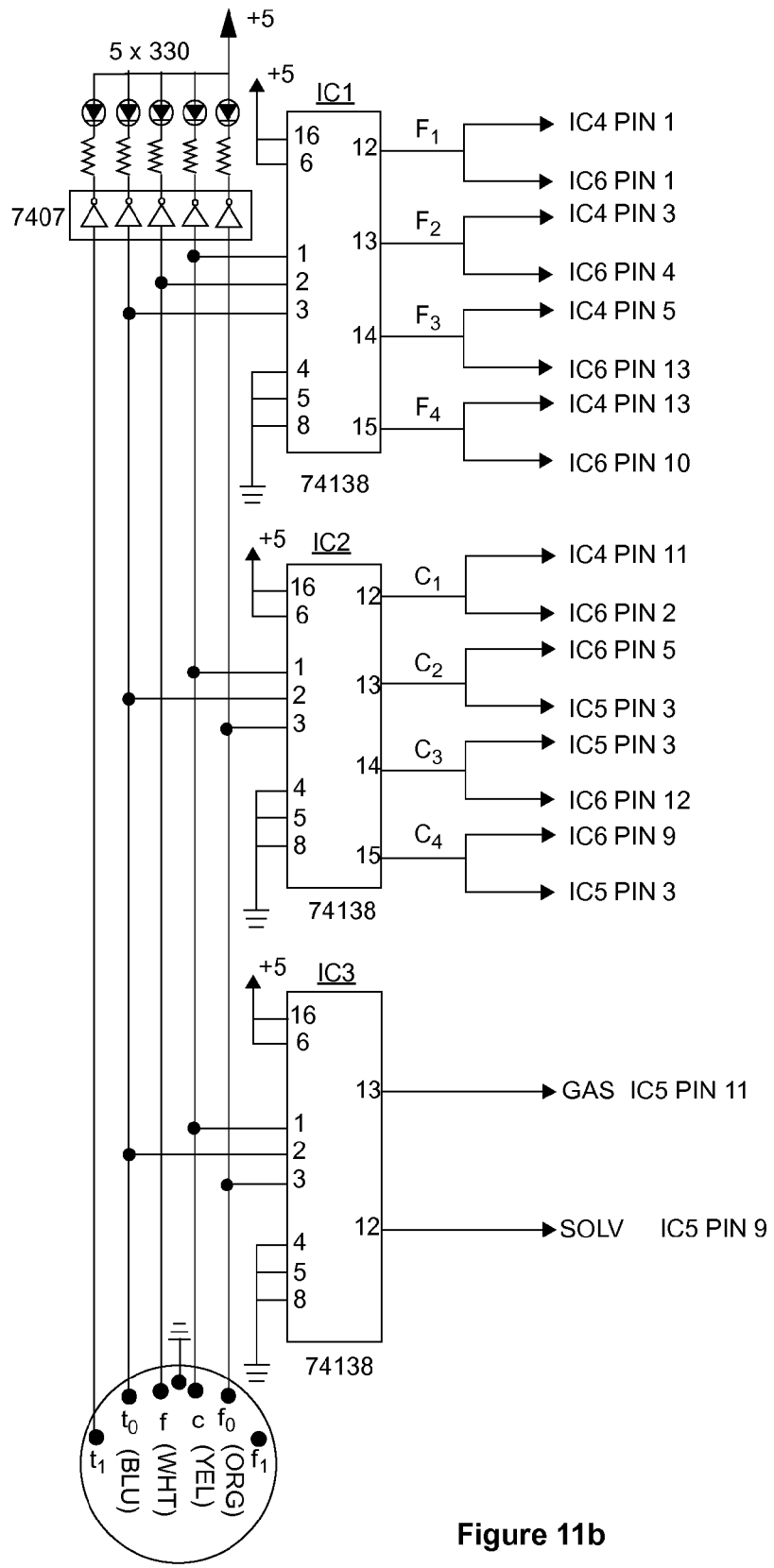
Figure 11C:
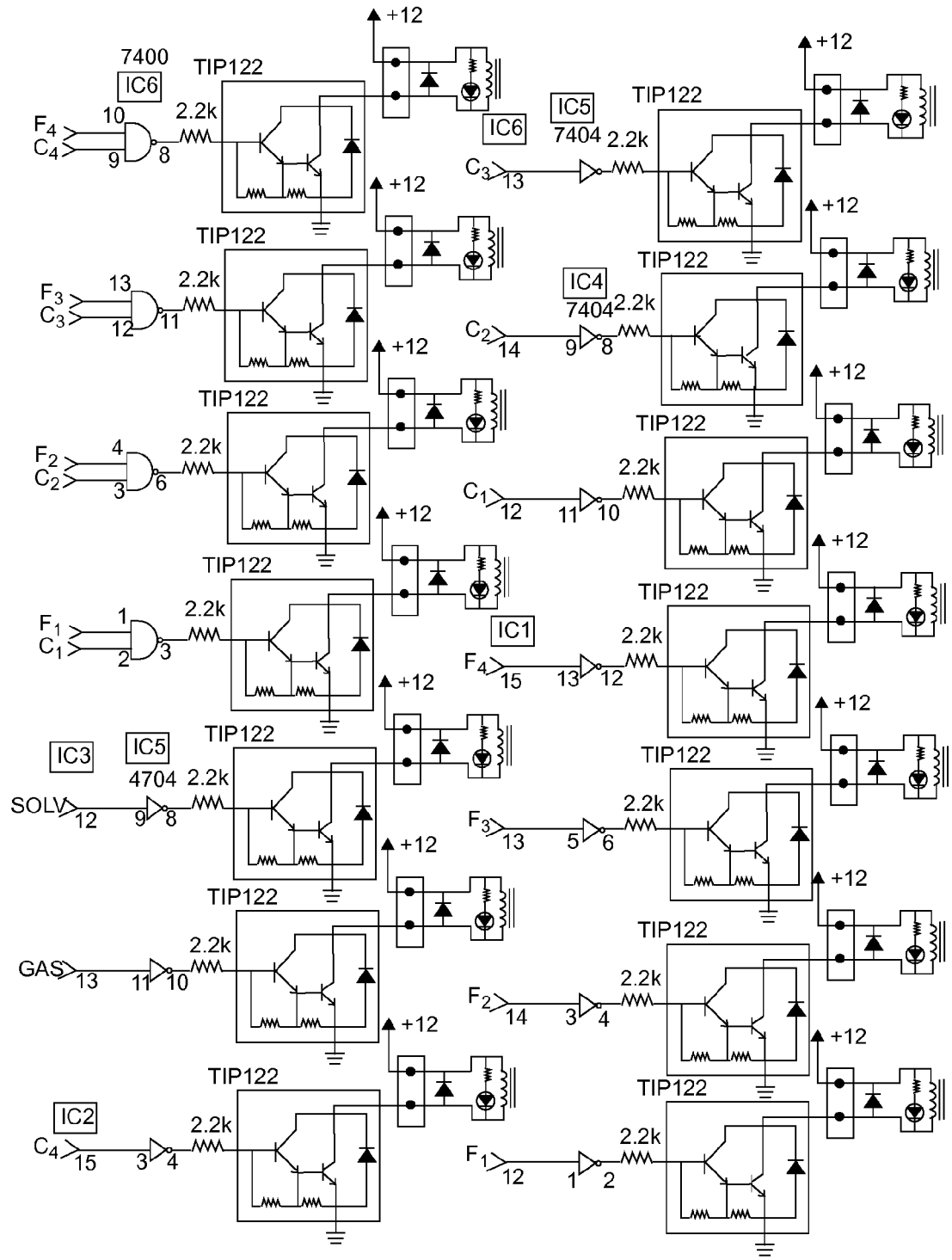

FIG. 10a shows an exemplary fluidic path implementation of a n: 1 input valve complex. This realization has provisions for clearing and drying with a clearing gas and cleaning with a liquid solvent. FIGS. 10b and 10c show an exemplary (n=4) electronic implementation of a 4:1 input 11-valve complex. Various colored LEDs may be provided, as provided in the figure, to show valve flow status. FIG. 11a shows an exemplary fluidic path implementation of a n:n input valve complex for multiport reaction chambers. This realization has provisions for clearing and drying with a clearing gas and cleaning with a liquid solvent. FIGS. 11b-11c shows an exemplary (n=4) electronic implementation of the 4:4 input 14-valve complex. Various colored LEDs may be provided, as provided in the figure, to show valve flow status.

Figure 12A:
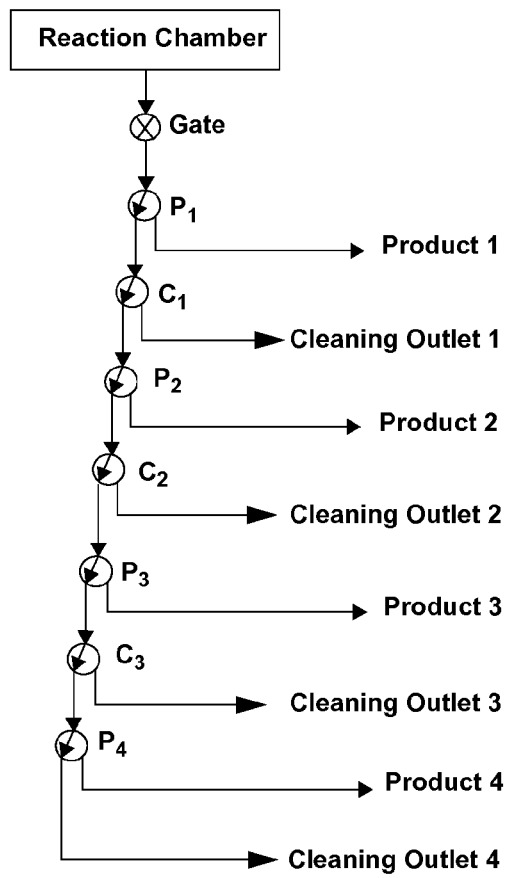
FIG. 12a shows an exemplary fluidic path implementation of a tandem 1:4 output (7+1) valve complex utilizing a cascade of single-pole single-throw ("SPDT") valves.
Figure 12B:
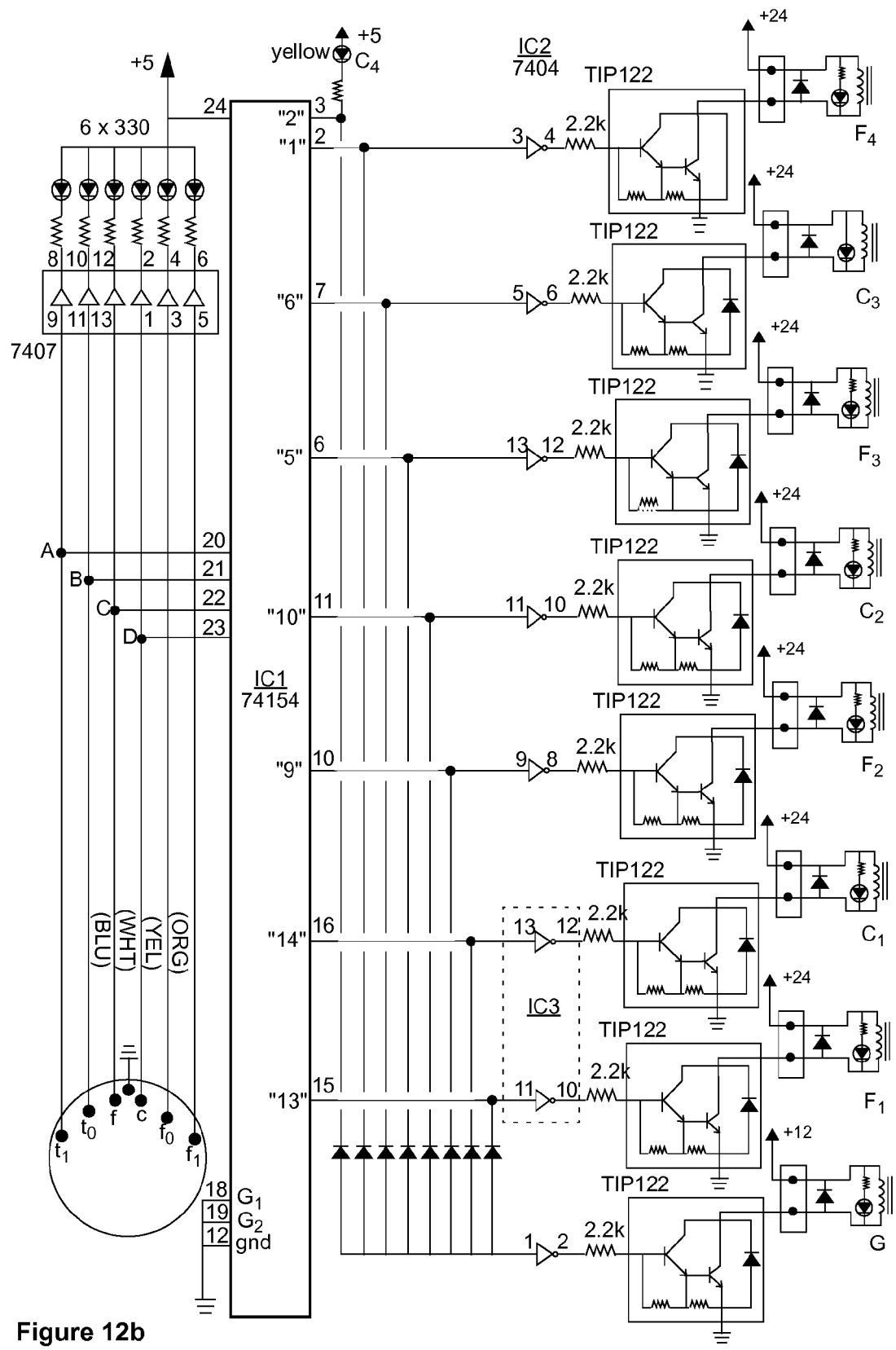
Figure 12C:
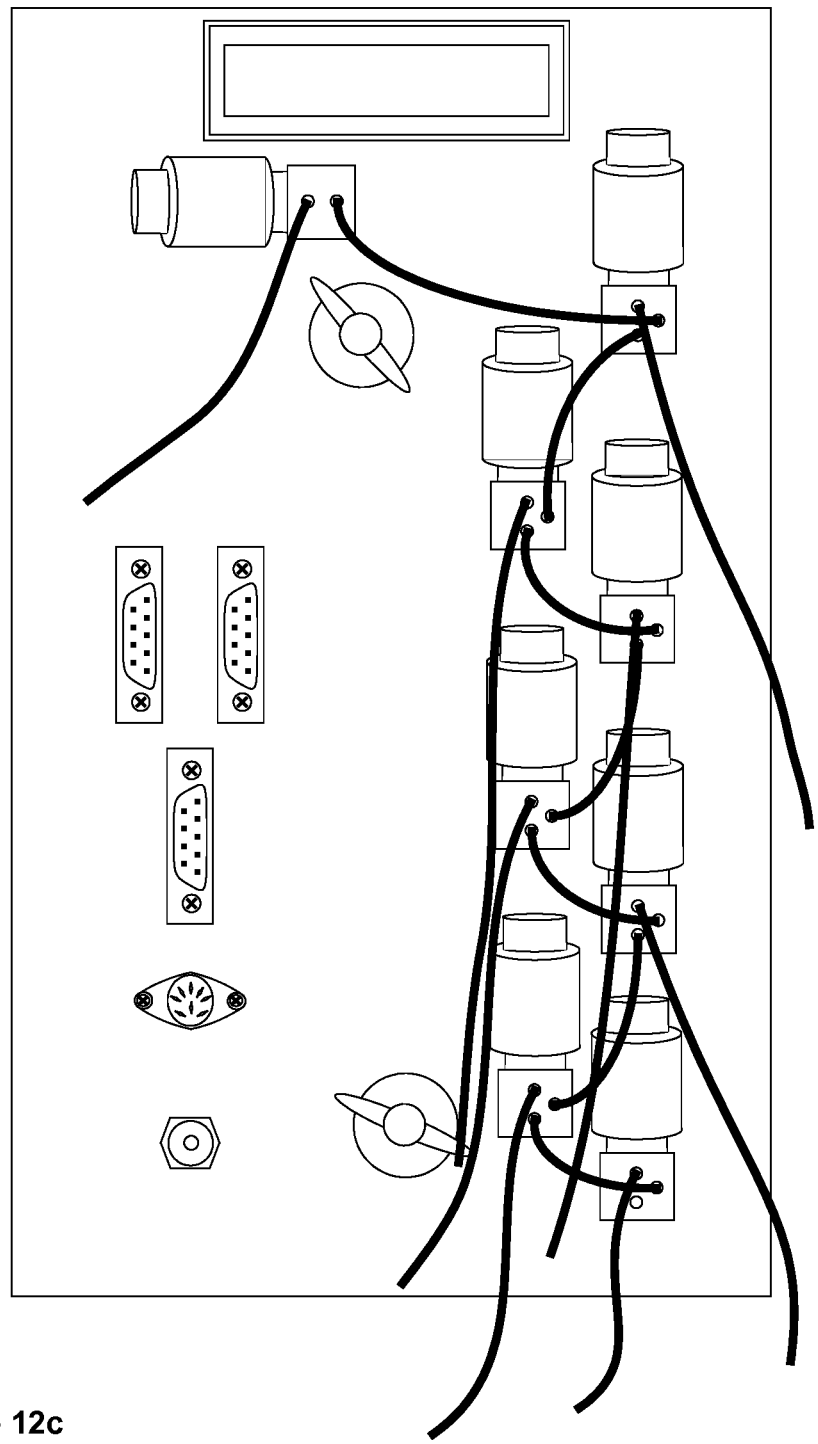
FIG. 12c shows a primitive exemplary hand-configurable laboratory lattice-scale implementation of the arrangement of FIGS. 12a-12b in a style similar to that of FIG. 8.

Exemplary Reconfigurable Fluidic/Gas Selection and Distribution Modules Supporting Clearing and Cleaning and Employing SPDT Valve Cascades FIG. 12a shows an exemplary fluidic path implementation of a 1:4 output (7+1) valve complex. This arrangement utilizes single-pole single-throw ("SPDT") valve cascade for distribution from, for example a reaction vessel, and has four separate cleaning outlets. FIG. 12b shows an exemplary electronic implementation of the 1:4 output (7+1) valve complex. Various colored LEDs may be provided, as provided in the figure, to show valve flow status. Other flow management and electrical approaches are possible as is clear to one skilled in the art and these are provided for by the invention. FIG. 12c shows an exemplary hand-configurable laboratory lattice-scale implementation of a style similar to that of FIG. 8a.

Figure 13A:
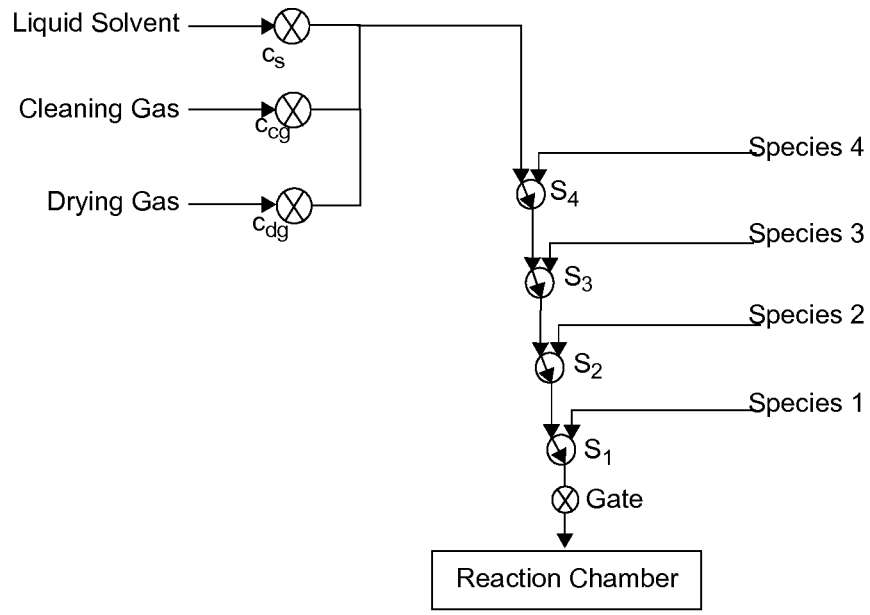
FIG. 13a shows an exemplary fluidic path implementation of a 4:1 input tandem selection valve complex employing a SPDT valve cascade with separate provisions for clearing and drying with a clearing gas and cleaning with a liquid solvent
Figure 13B:
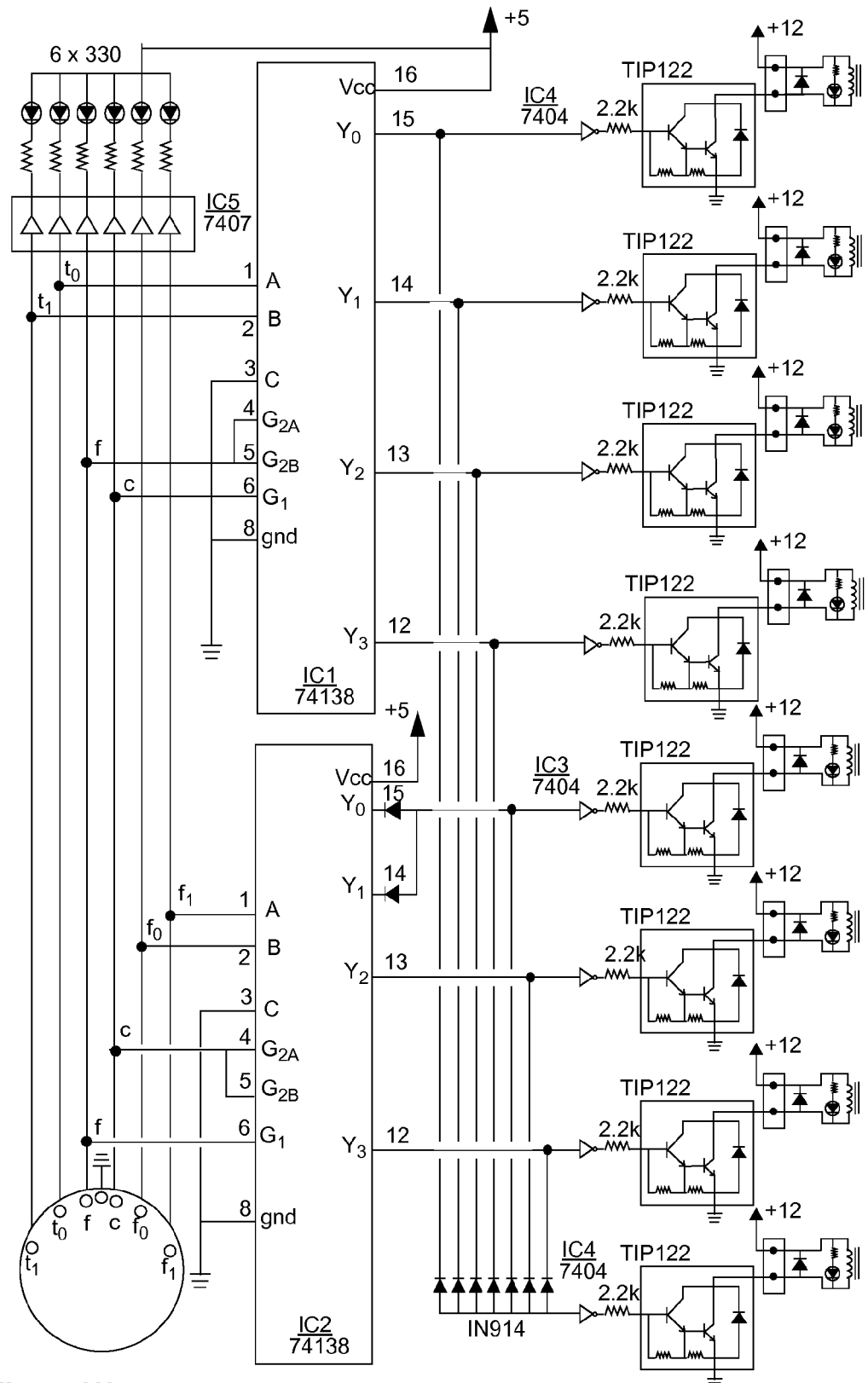

FIG. 13a shows an exemplary fluidic path implementation of a 4:1 input tandem valve complex. It is a selection valve complex using "SPDT" valve cascade with separate provisions for clearing and drying with a clearing gas and cleaning with a liquid solvent. FIG. 13b shows an exemplary electronic implementation of the 4:1 input tandem valve complex. Various colored LEDs may be provided, as provided in the figure, to show valve flow status.

Figure 14A:
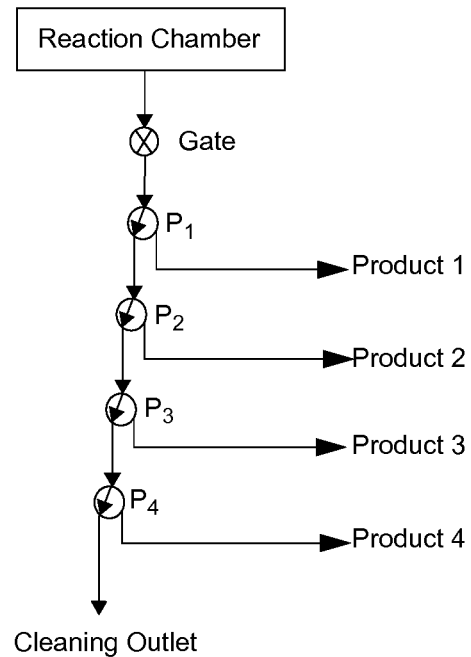
FIG. 14a shows an exemplary fluidic path implementation of a 4:1 tandem output distribution valve complex employing a SPDT valve cascade.
Figure 14B:
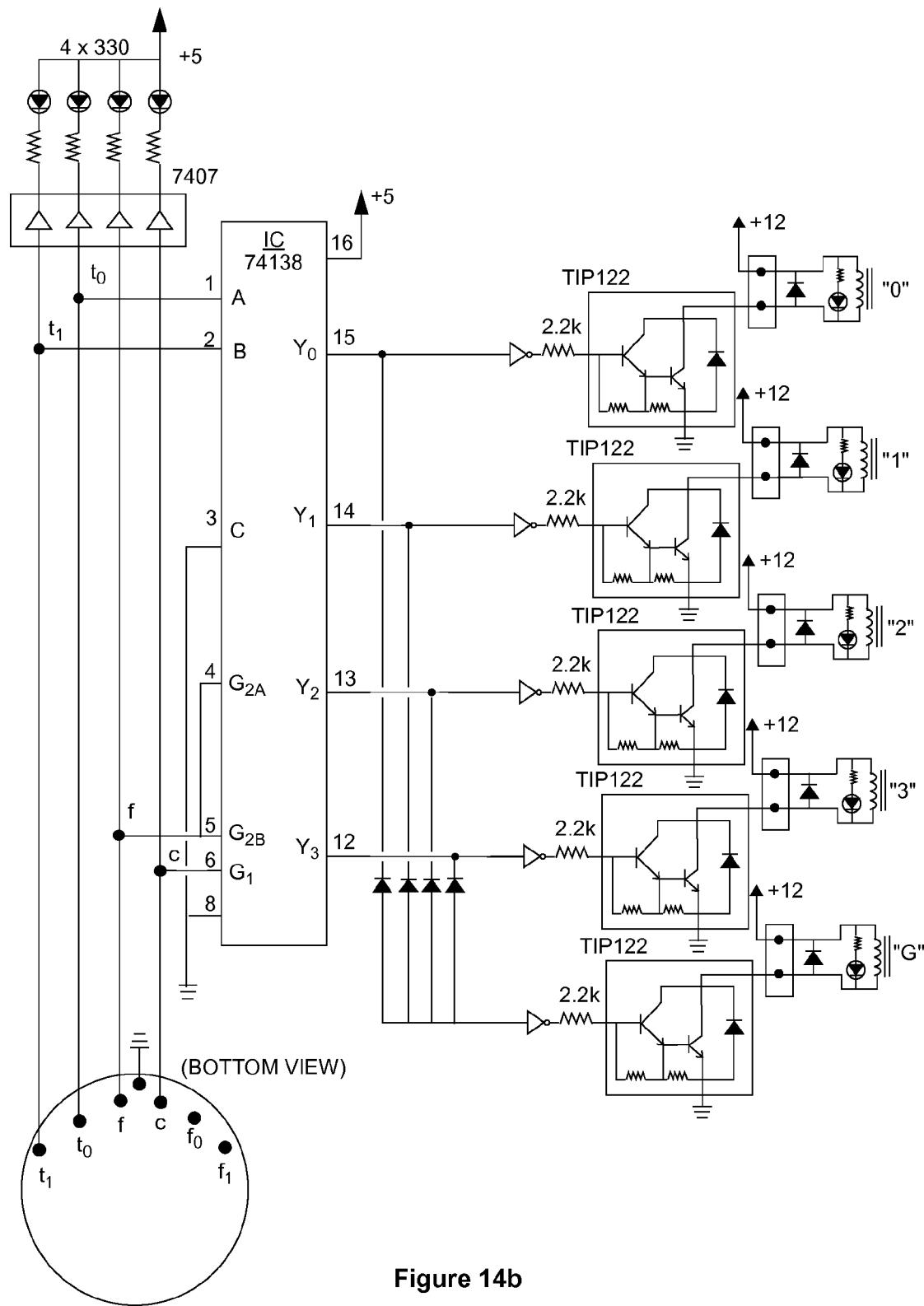

FIG. 14a shows an exemplary fluidic path implementation of a 4:1 tandem output valve complex. FIG. 14b shows an exemplary electronic implementation of the 4:1 tandem output valve complex. Various colored LEDs may be provided, as provided in the figure, to show valve flow status. Other flow management and electrical approaches are possible as is clear to one skilled in the art and these are provided for by the invention.

Exemplary Controllable Pressure and Venting Systems

In order for flows to occur there typically must be pressure differences or gradients within the configured system and/or any external connections outside the configured system. In some embodiments, these pressure differences or gradients may provide the means for propelling transported substances and materials within an LoC and emulated system, and as such may be created or modulated by pumps, valves, chemical reactions, or other techniques. In other embodiments, the propelling transported substances and materials may involve other transport processes, such as microchannel osmosis or electrokinetic flow in LoC systems. In such circumstances pressure differences or gradients within the larger associated system and/or any external connections are created as a result of transport processes.

In either case, pressure equalization and/or venting may be required in order for the flows of liquids and gasses to occur. In some embodiments, pressure equalization and/or venting may be accomplished by a Multi-channel Chemical Transport Bus described later. In other embodiments, separate provisions devoted to pressure equalization and/or venting functions are provided.

In many circumstances venting complements fluid or gas transport valve operations, so it is often convenient to "slave" the venting valves from the same signals used to control corresponding fluid or gas transport valve operation.

Figure 15A:
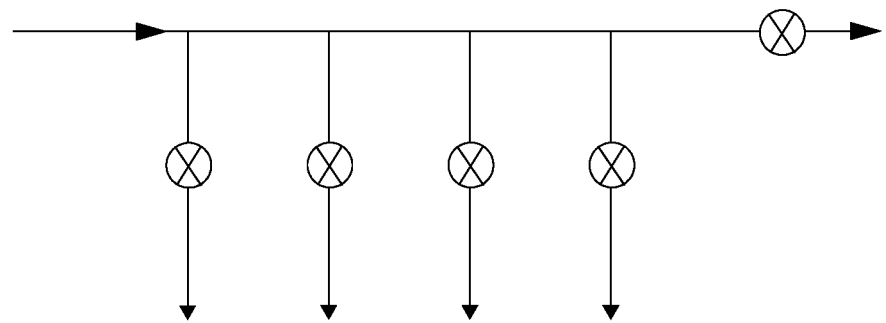
FIG. 15a shows an exemplary fluidic path implementation of a 4-port gas routing 5-valve complex that may be used for venting, pressure and gas distribution.

FIG. 15a shows an exemplary fluidic path implementation of a 4-port gas routing 5-valve complex that may be used for venting, pressure and gas distribution. A venting or "outflow" valve is depicted on the right; this valve opens when any individual vent valve is opened. A cascading port is depicted on the left; this may be used to add additional stages (for example when creating a venting bus), or may be plugged, or may be left open to passively defeat the "outflow" valve in more complex venting embodiments.

Figure 15B:
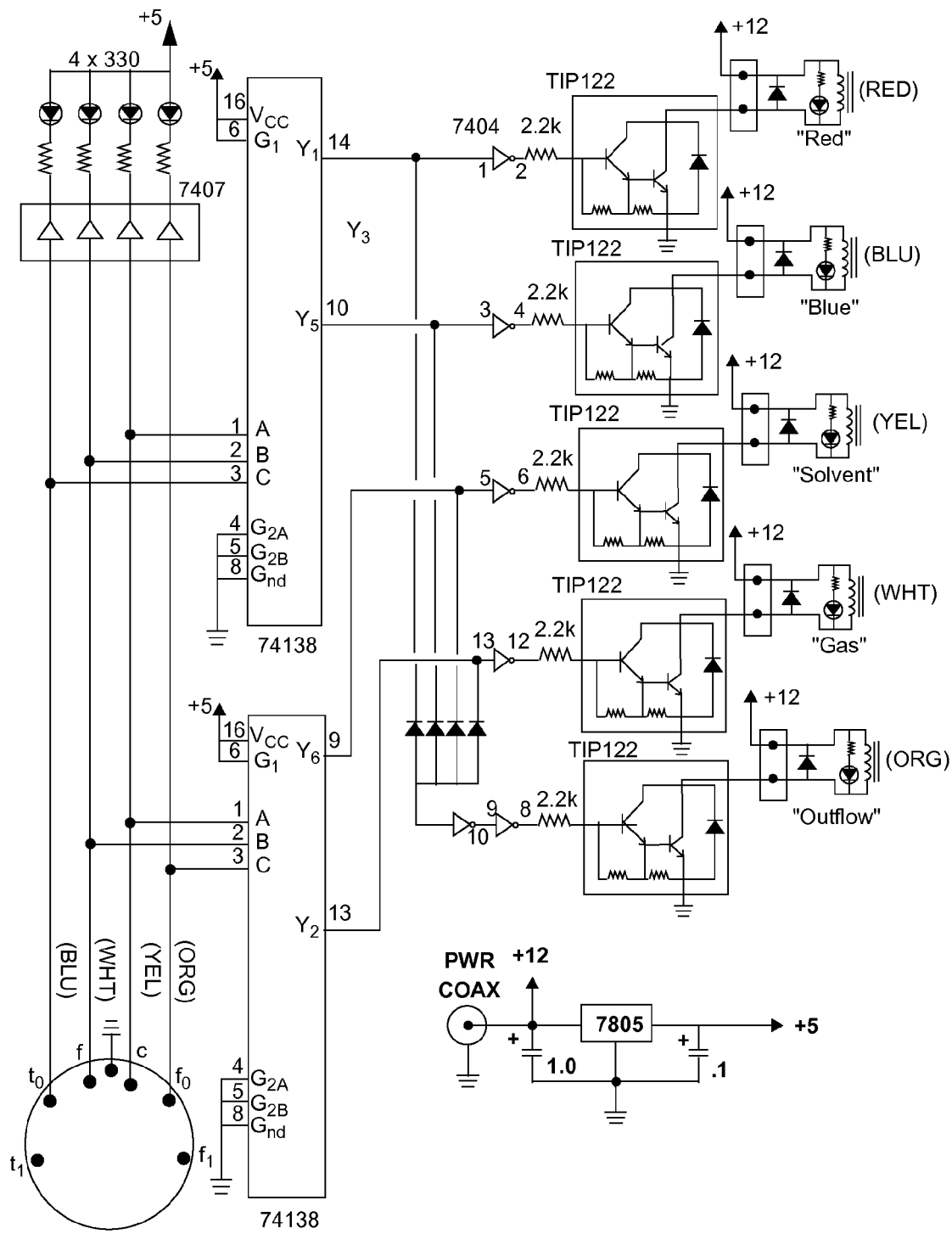

FIG. 15b shows an exemplary slaved electronic implementation of the 4-port gas routing 5-valve complex. In this arrangement logic circuitry is provided to ensure only one venting port is open at a time, and the "outflow" valve also opens when any individual vent is open. Various colored LEDs may be provided, as provided in the figure, to show valve flow status.

Figure 16A:
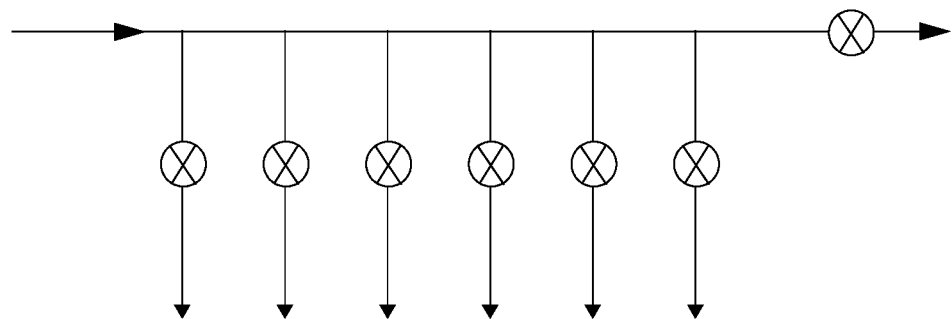
FIG. 16a shows an exemplary fluidic path implementation of a gas routing 7-valve complex, similar to that of FIG. 15a but with 6 vent/pressure ports rather than 4.
Figure 16B:
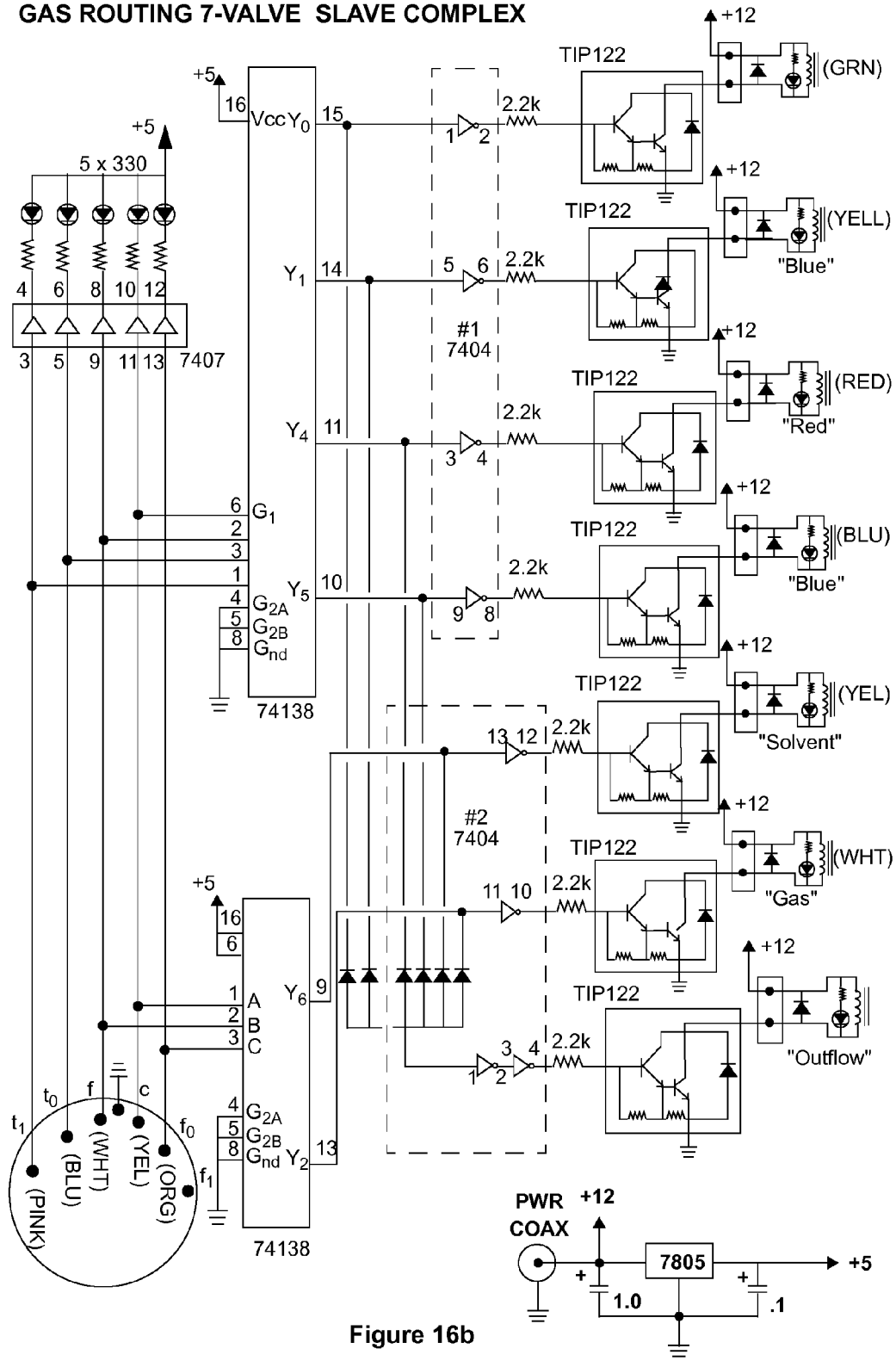

FIG. 16a shows an exemplary fluidic path implementation of a 6-port gas routing 7-valve complex. This arrangement is similar to that of FIG. 15a but with 6 vent/pressure ports rather than 4. FIG. 16b shows an exemplary slaved electronic implementation of the slaved gas routing 7-valve complex. Various colored LEDs may be provided, as provided in the figure, to show valve flow status.

Exemplary Block Fluidic/Gas Valve Modules

A number of manufactures provide valve "block" products commonly used in HPLC systems. These products typically include high-performance low-voltage electrically-operated solenoid valves mounted on a common block of Teflon® PTFE or other chemical-resistant material. The fluidic/gas flow ports are typically threaded with a standard NPT threading. These products will be referred to herein as "block valves."

Various types of such block valves may be used for a wide range of purposes, including interfacing with HPLC systems in laboratory automation applications. In emulation systems, they may be used as selection valves, distribution valves, pressure equalization/venting valves, and as tap elements in the multi-channel chemical transport buses described later.

Figure 17A:
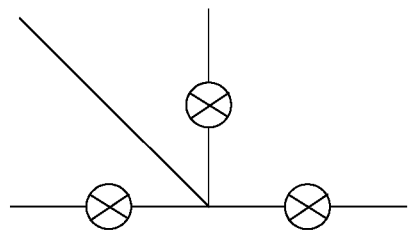
FIG. 17a shows an exemplary fluidic path implementation of a 3:1 block valve that may be used for a variety of general purposes.
Figure 18A:
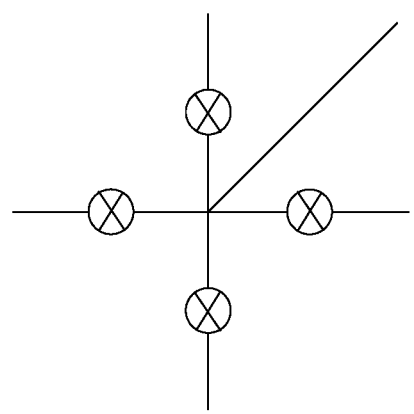
FIG. 18a shows an exemplary fluidic path implementation of a 4:1 block valve that is used for general purposes.
Figure 17B:
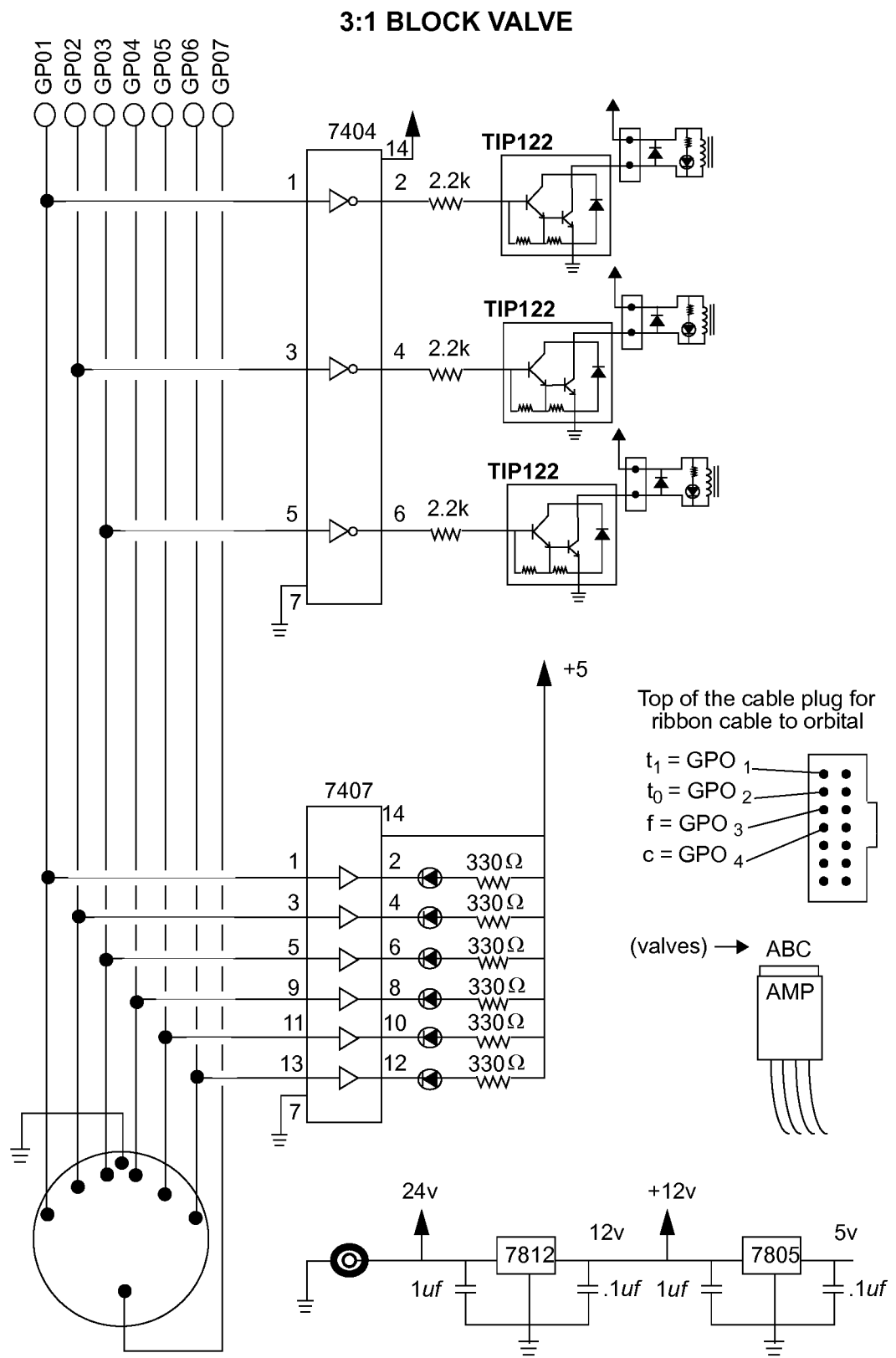
FIG. 17b shows an exemplary electronic implementation of the 3:1 block valve.
Figure 18B:
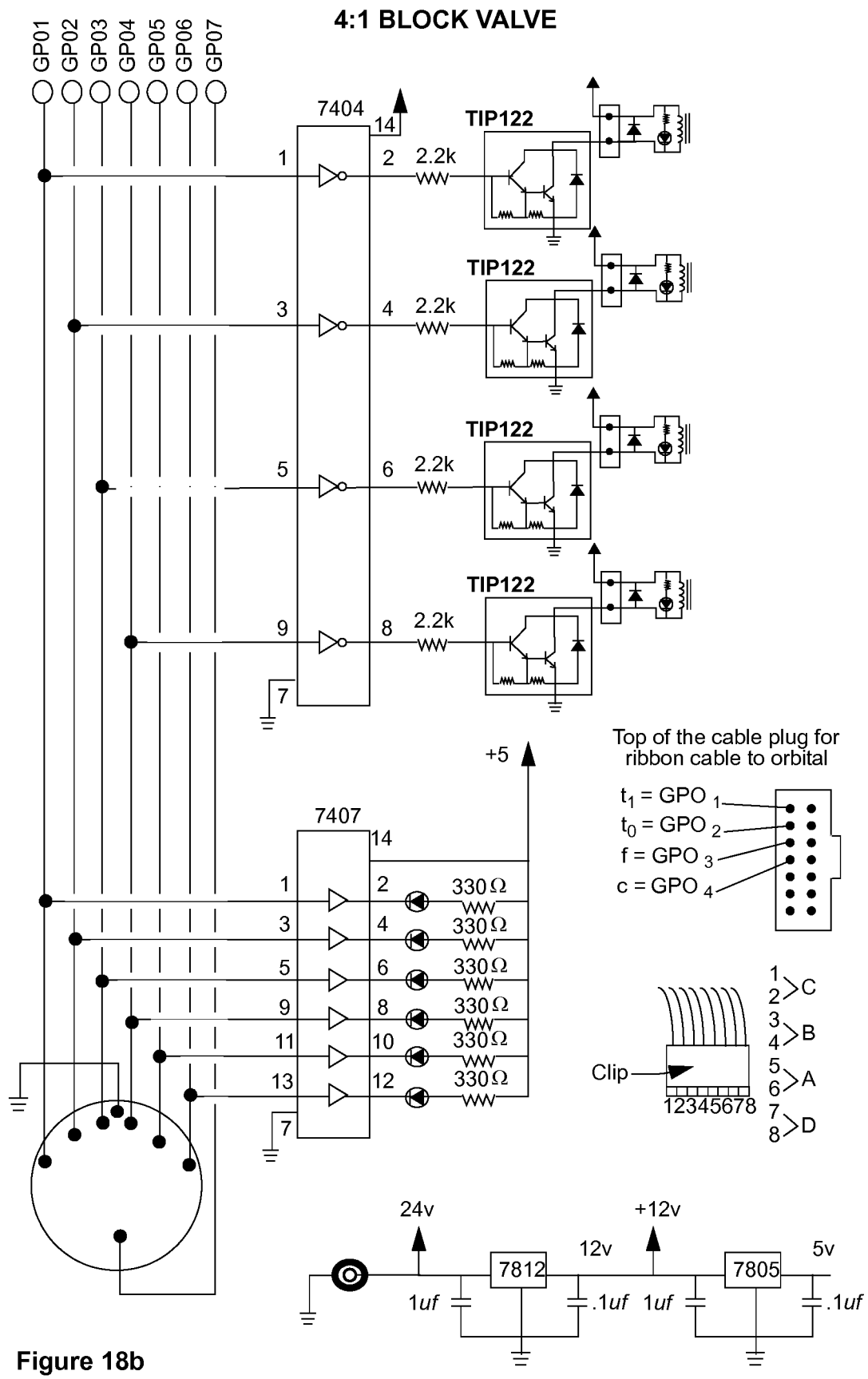
FIG. 18b shows an exemplary electronic implementation of the 4:1 block valve.
Figure 19:
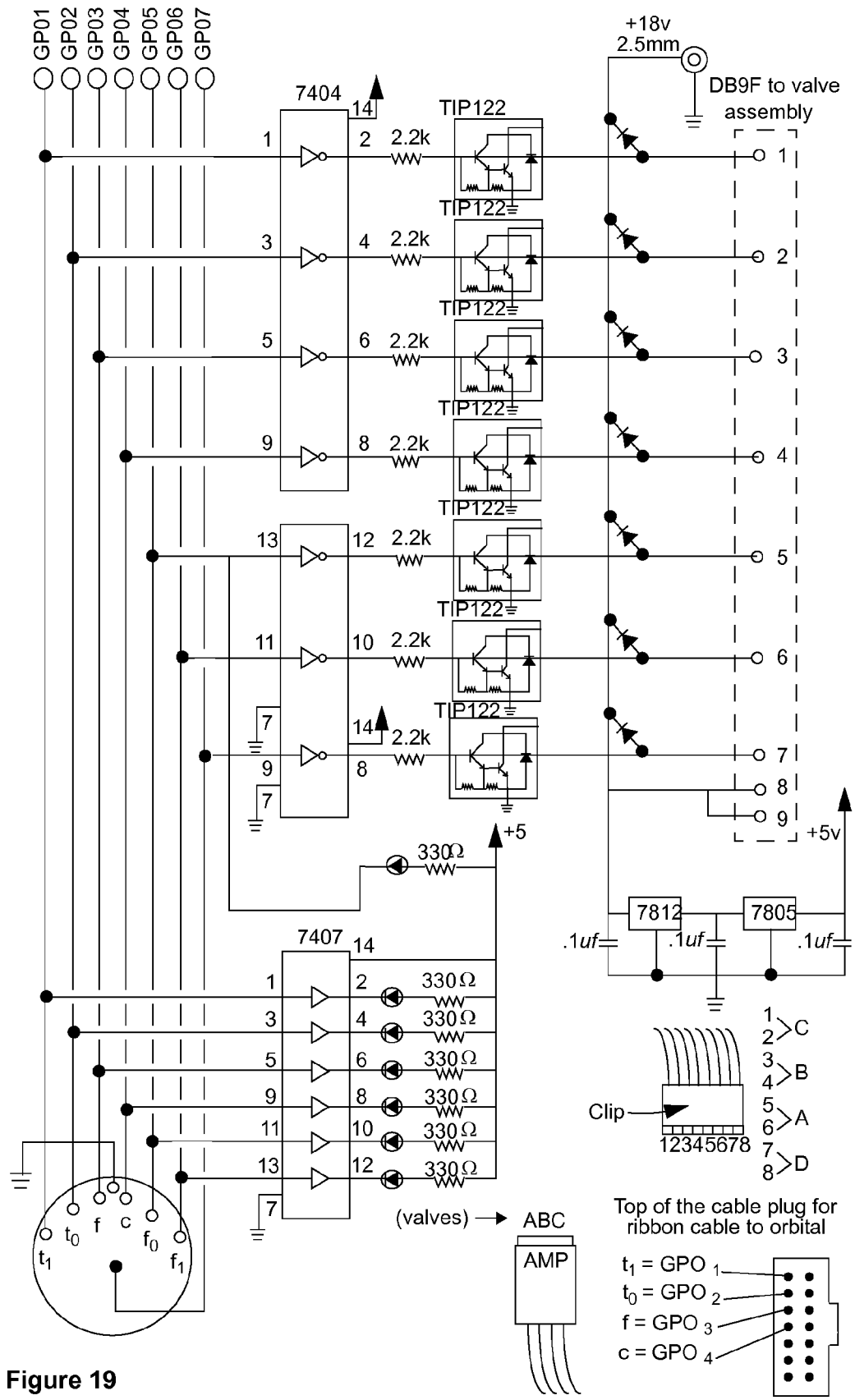
FIG. 19 shows an exemplary combined electronic implementation of the 4:1 block valve together with 3:1 block valve.

FIG. 17a shows an exemplary fluidic path implementation of a 3:1 block valve that may be used for a variety of general purposes. FIG. 17b shows an exemplary electronic implementation of the 3:1 block valve. FIG. 18a shows an exemplary fluidic path implementation of a 4:1 block valve that is used for general purposes. FIG. 18b shows an exemplary electronic implementation of the 4:1 block valve. As the number of output ports employed in the electronics depicted in each of FIGS. 17b and 18b is relatively small, it may be advantageous in some embodiments to combine with other valves, pumps, or other items. As an example, FIG. 19 shows an exemplary combined electronic implementation of the 4:1 block valve together with 3:1 block valve. In each of FIGS. 17b, 18b, and 19, various colored LEDs may be provided, as provided in the figure, to show valve flow status.

Figure 20:
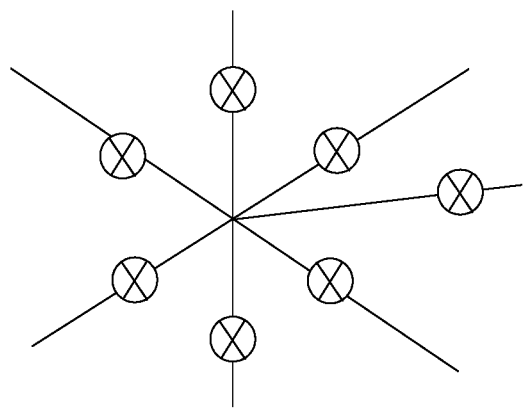
FIG. 20 shows an exemplary fluidic path implementation of a 6:1+1 block valve that is for general purposes or for use as part of a chemical transport bus.
Figure 21:
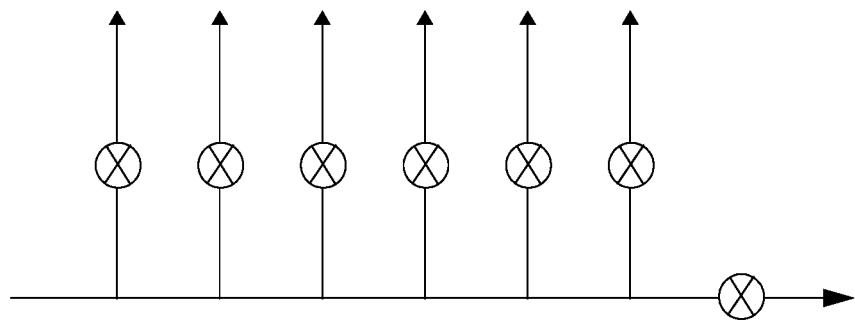
FIG. 21 shows an exemplary fluidic path implementation of a 6:1 block Manifold Valve that is for general purposes or for use as part of a chemical transport bus.
Figure 22:
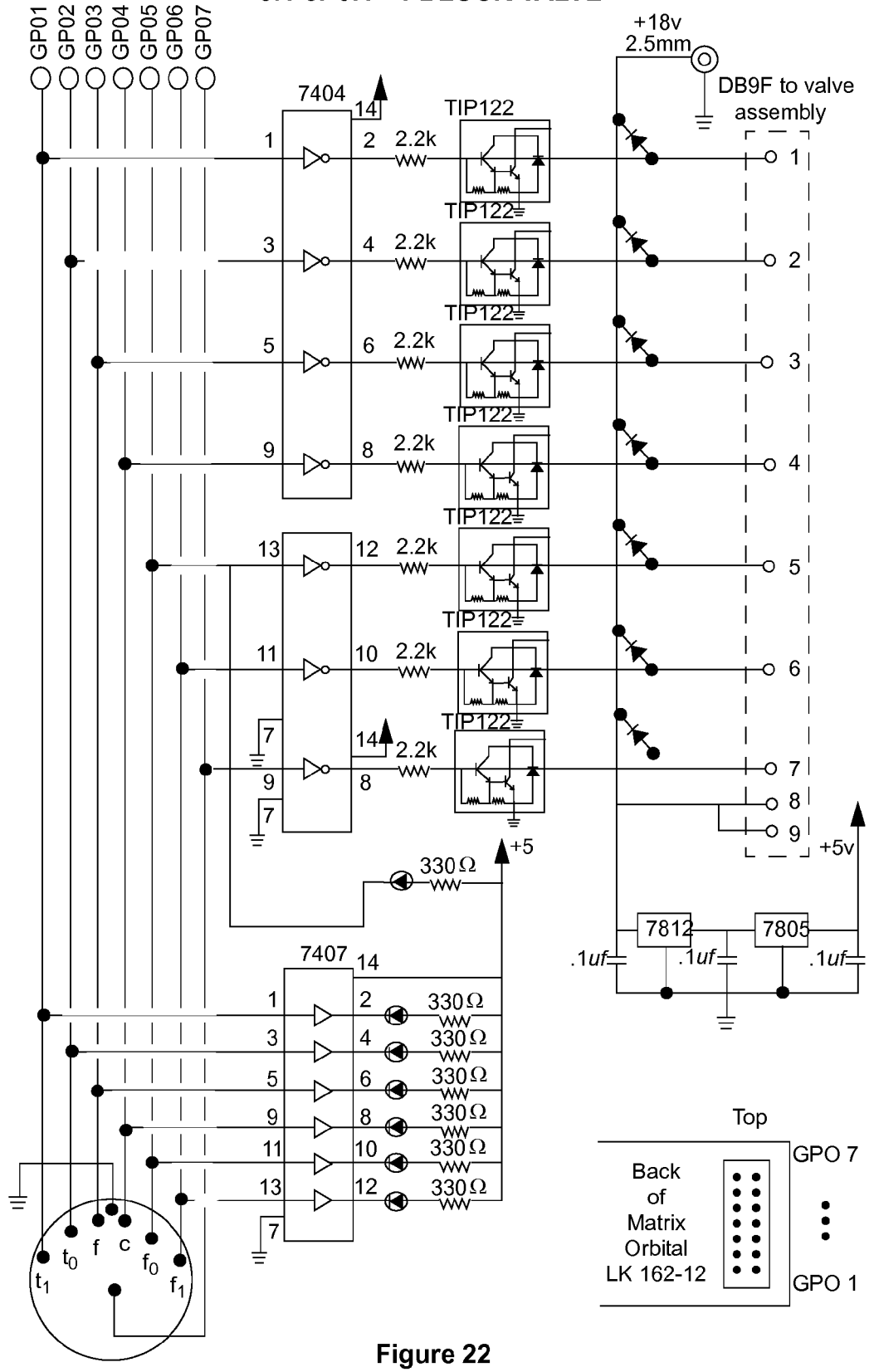
FIG. 22 shows an exemplary electronic implementation that can be used for either the 6:1+1 block valve of FIG. 20 or the 6:1 block manifold valve of FIG. 21.

FIG. 20 shows an exemplary fluidic path implementation of a 6:1+1 block valve that is for general purposes or for use as part of a chemical transport bus. FIG. 21 shows an exemplary fluidic path implementation of a 6:1 block Manifold Valve that may be used for general purposes or for use as part of a chemical transport bus (described below). FIG. 22 shows an exemplary electronic implementation that can be used for either the 6:1+1 block valve of FIG. 20 or the 6:1 block manifold valve of FIG. 21. Various colored LEDs may be provided, as provided in the figure, to show valve flow status.

Multi-Channel Chemical Transport Bus

If desired, an embodiment may include for incorporation of a Multi-channel Chemical Transport Bus as a reconfigurable chemical process emulation system or other reconfigurable chemical process system. Applicable methods and systems for a Multi-Channel Chemical Transport Bus that may be directed to the physical scale pertinent to embodiments of the invention are provided in provisional U.S. patent application entitled "Multi-Channel Chemical Transport Bus for Microfluidic and Other Applications" Ser. No. 61/005,429, filed Dec. 4, 2007, and the patent application entitled "Multi-Channel Chemical Transport Bus for Microfluidic and Other Applications" filed concurrently herewith (Atty. Docket No. 2152-3059) and which also claims benefit of priority of application Ser. No. 61/005,429.

Exemplary Pump Module

FIG. 24 shows an exemplary laboratory lattice-scale embodiment of a variable speed pump module having two variable-speed low-voltage DC motor diaphragm pumps and four chaperoning routing/switch valves. These elements may also be implemented at smaller scales in a similar fashion. These elements may be operated by the exemplary electrical circuit of FIG. 23. Here the variable speed DC motors are provided high-current variable voltage (selected by an analog switch from the wipers of panel potentiometers). Alternatively, DACs may be used in place of potentiometer voltage references and analog switches. Additionally, analog and bus communications electronics may be included to provide read-back of sensor measurements as described earlier.

Various colored LEDs may be provided, as provided in the figure, to show pump activity and valve flow status. In the Figure, LEDs brightness varies with applied voltage that determines the pump flow rate.

Exemplary Reconfigurable Chemical Reactor Module

At the heart of most reconfigurable chemical processing systems are various types of chemical processing elements and sensors. These can widely vary. In a reconfigurable chemical processing systems used to emulate fixed, configurable, or reconfigurable LoCs, the reconfigurable chemical processing system will be provided with one or more types of reconfigurable chemical reactor modules.

FIG. 25a shows an exemplary glassware element that can be used in a laboratory lattice-scale implementation of a chemical reactor module. Smaller-scale implementations may use smaller glass vessel, cavities in PTFE materials, etc. This exemplary glassware element comprises a gas bubbler, liquid-flow thermal jacket, open top for stoppers providing various immersible inlet/outlet tubes, sensor complexes, electrochemistry electrodes, etc., a side fill-inlet at the top, a secondary reaction array with a side inlet, and drain port. The friction-fit stopper may be additionally secured with clamps or adhesives to withstand enhanced pressures within the glassware vessel. Of course a wide arrange of other possible elements could be used in place of the exemplary element described herein.

Figure 25C:
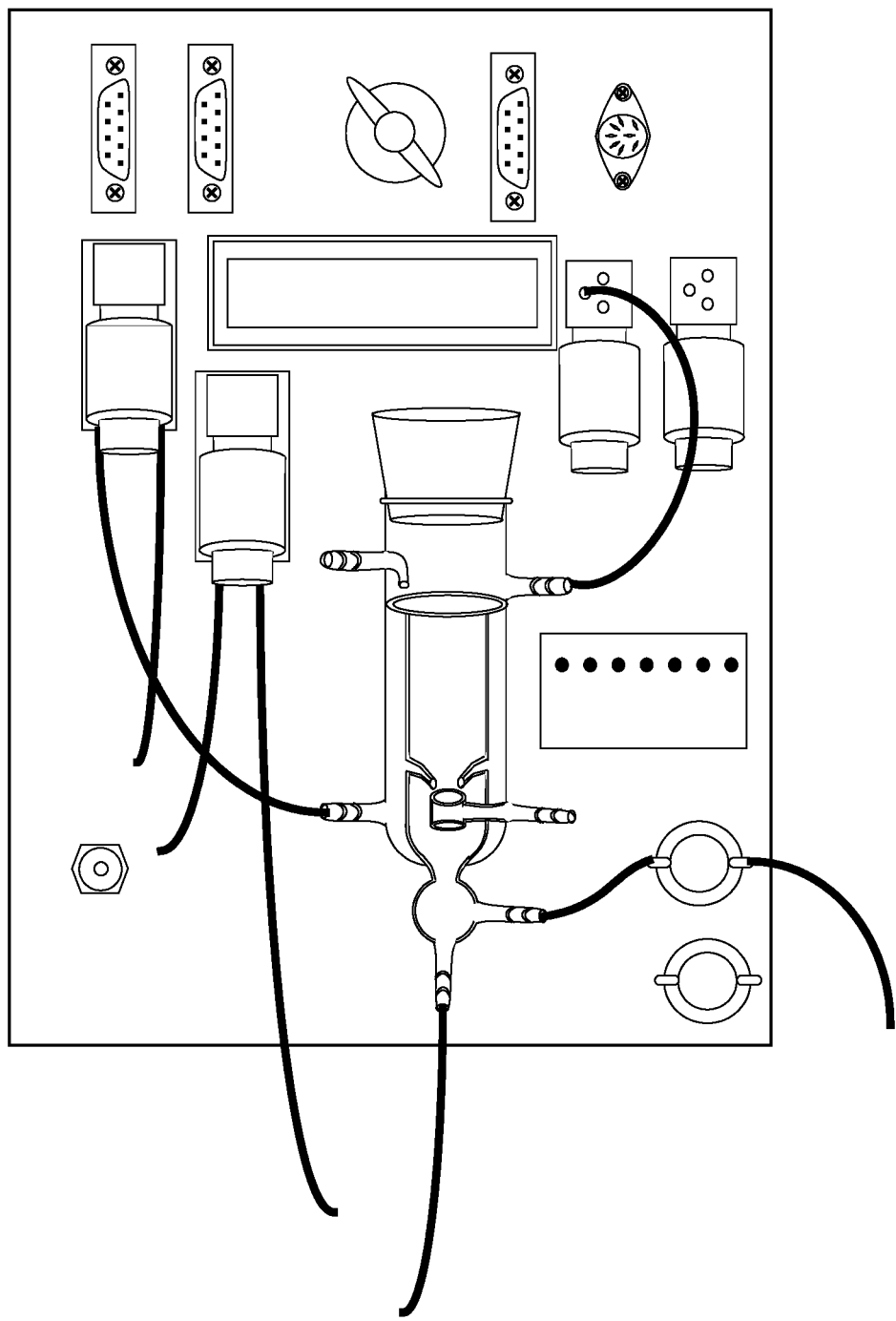

Continuing with an exemplary laboratory lattice-scale implementation of a chemical reactor module, the exemplary glassware element is further provided with reaction controlling and monitoring elements, such as pumps, valves, and heating elements. FIG. 25b shows an exemplary laboratory lattice-scale mechanical and electronic support implementation for the chemical reactor module based on the exemplary glassware element of FIG. 25a. In one embodiment, thermal regulation is provided by controlled mixtures of warmer and cooling fluids circulating through the thermal jacket. These items may be controlled by circuitry such as that depicted in FIG. 23 or other alternate of more specific electronics. Additionally, analog and bus communications electronics may be included to provide read-back of sensor measurements as described earlier. FIG. 25c depicts a primitive exemplary hand-configurable laboratory lattice-scale implementation combining the exemplary glassware element of FIG. 25a with the arrangement of FIG. 25b in a style similar to that of FIG. 8.

Exemplary On/Off Electrical Controller

Figure 26:
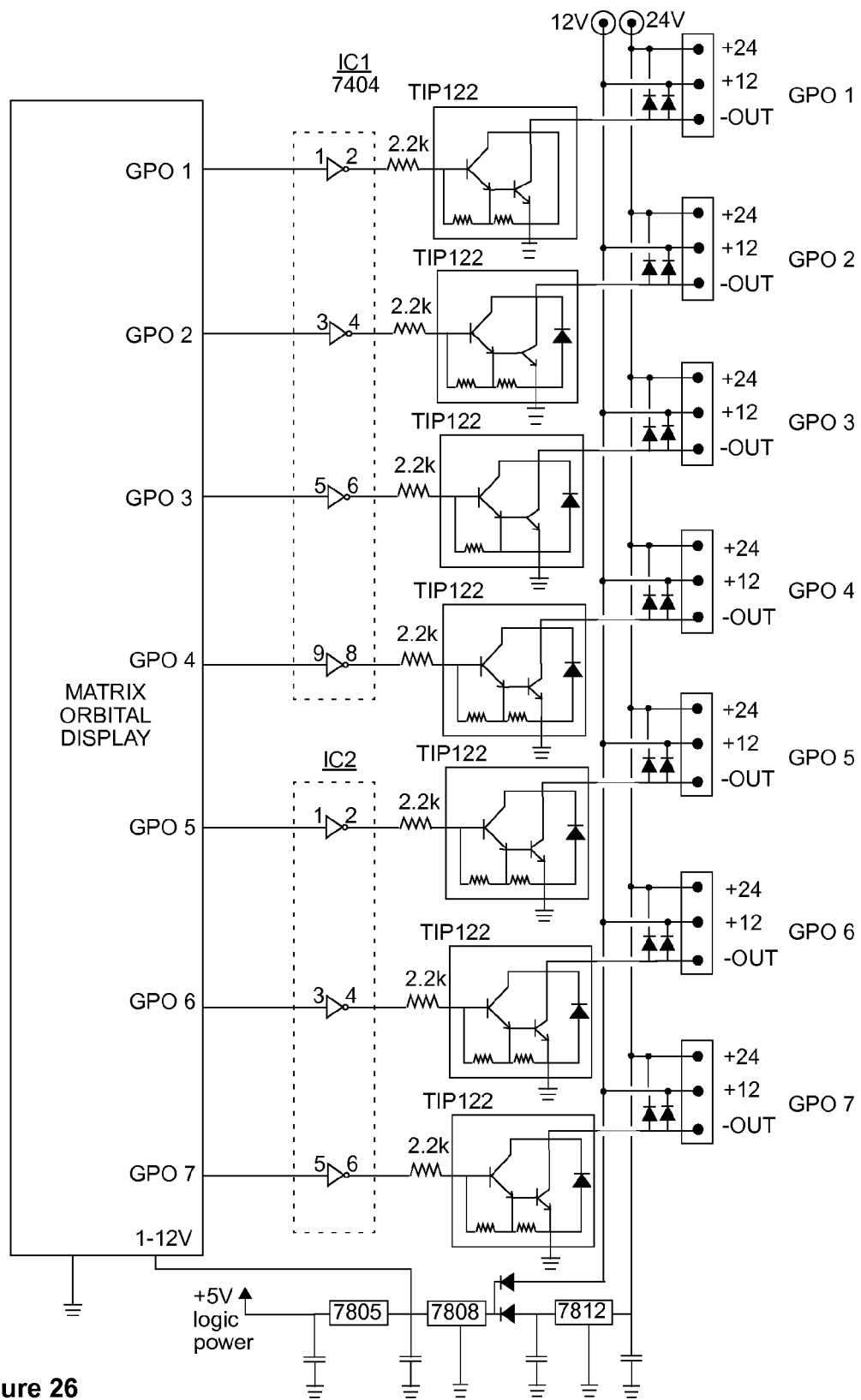
FIG. 26 shows an exemplary electronic implementation of a General Purpose 7-Channel Dual-Voltage Controller.

FIG. 26 shows an exemplary electronic implementation of a general purpose 7-Channel Dual-Voltage Controller. Controls of low current loads include 12 volt, 24 volt, or other voltage levels. Protection diodes are provided for inductive loads. This sort of general purpose electrical controller may be used to interface various peripheral items and elements of other connected external systems such a HPLC valves and mixers. Other approaches for such a controller are possible as is clear to one skilled in the art. Additionally, analog and bus communications electronics as described earlier may be included to provide analog output voltages and/or read-back of sensor measurements.

It is understood that various techniques for flow management circuitry designed have been described. However, other flow management and electrical approaches are possible in accordance with assorted embodiments of the present invention.

While the invention has been described in detail with reference to disclosed embodiments, various modifications within the scope of the invention will be apparent to those of ordinary skill in this technological field. It is to be appreciated that features described with respect to one embodiment typically may be applied to other embodiments. Therefore, the invention properly is to be construed with reference to the claims.

What is claimed is:

1. A system for emulating a lab-on-a-chip design, the system comprising:
a plurality of electrically-powered controllable chemical process modules, the chemical process modules being of laboratory lattice-scale, each chemical process module for implementing at least one chemical reaction and comprising
at least one chemical flow input port,
at least one chemical flow output port,
at least one communications interface employing a communications protocol and receiving communications signals, and
at least one electrically controllable element responsive to received communications signals;
chemical flow interconnections among at least a first and a second of the chemical process modules, the chemical flow interconnections comprising a chemical flow path connecting the chemical flow output port of a first chemical process module with a second chemical process module; and a network for carrying communications signals, the network connecting with the communications interface of the first chemical process module and with the communications interface of the second chemical process module, the network additionally providing a connection to a data processor, the data processor for executing algorithms for controlling the at least one electrically controllable element of each of the first and second chemical process modules;

wherein the chemical process modules are controlled by an algorithm executed by the data processor to emulate aspects of at least one lab-on-a-chip;

wherein each chemical process module is configured to be addressed via the at least one communications interface to implement the algorithm;

wherein the chemical process modules and the chemical flow interconnections perform a chemical process that emulates aspects of the at least one lab-on-a-chip using the algorithm and numerical models;

wherein the chemical process modules, the chemical flow interconnections, and the algorithm are configured to be reconfigurable to emulate at least portions of more than one type of lab-on-a-chip.

2. The system of claim 1 wherein at least one of the plurality of chemical process modules is configured to be mounted on standard laboratory stands.

3. The system of claim 1 wherein at least one of the plurality of chemical process modules is configured to be mounted on standard laboratory lattices.

4. The system of claim 1 wherein at least one of the plurality of chemical process modules is configured to permit hand customizations.

5. The system of claim 1 wherein at least one chemical flow input port of the first of the plurality of controllable chemical process modules supports fluid flow.

6. The system of claim 1 wherein at least one chemical flow input port of the first of the plurality of controllable chemical process modules supports gas flow.

7. The system of claim 1 wherein at least one chemical flow input port of the first of the plurality of controllable chemical process modules supports mixed-media flow.

8. The system of claim 1 wherein at least one chemical flow input port of the first of the plurality of controllable chemical process modules supports vapor flow.

9. The system of claim 1 wherein the communications network comprises a sequential daisy-chain interconnection among the first and the second controllable chemical process modules.

10. The system of claim 1 wherein the communications protocol comprises self-clocking bidirectional serial communications.

11. The system of claim 1 wherein the communications protocol operates on a parallel communications bus.

12. The system of claim 1 wherein at least the first chemical process module of the plurality of controllable chemical process modules is configured to include a temperature sensor.

13. The system of claim 1 wherein at least the first chemical process module of the plurality of controllable chemical process modules is configured to support clearing through use of a clearing gas.

14. The system of claim 1 wherein at least the first chemical process module of the plurality of controllable chemical process modules is configured to support cleaning through use of a cleaning solvent.

15. The system of claim 1 wherein at least the first chemical process module of the plurality of controllable chemical process modules includes at least one LED configured to show valve flow status.

16. The system of claim 1 wherein the first chemical process module and the second chemical process module comprise separated physical mounting arrangements.

17. The system of claim 1 wherein at least the first electrically-powered controllable chemical process module of the plurality of controllable chemical process modules comprises a motorized fluidic mixer.

18. The system of claim 1 wherein at least the first electrically-powered controllable chemical process module of the plurality of controllable chemical process modules comprises an electrically-operated pump.

19. The system of claim 1 wherein at least the first electrically-powered controllable chemical process module of the plurality of controllable chemical process modules comprises an electrically-operated valve.

20. The system of claim 1 wherein at least the first electrically-powered controllable chemical process module of the plurality of controllable chemical process modules comprises a reaction chamber.

* * * * *